(12) United States Patent
Herman et al.

(10) Patent No.: US 10,889,826 B2
(45) Date of Patent: Jan. 12, 2021

(54) METHODS AND COMPOSITIONS FOR PRODUCING EPIDERMAL GROWTH FACTOR (EGF) IN SOYBEANS

(71) Applicants: ARIZONA BOARD OF REGENTS ON BEHALF OF THE UNIVERSITY OF ARIZONA, Tucson, AZ (US); Washington University, St. Louis, MO (US)

(72) Inventors: Eliot Herman, Tucson, AZ (US); Monica Schmidt, Tucson, AZ (US); Brad W. Warner, St. Louis, MO (US)

(73) Assignees: ARIZONA BOARD OF REGENTS ON BEHALF OF THE UNIVERSITY OF ARIZONA, Tucson, AZ (US); WASHINGTON UNIVERSITY, St. Louis, MO (US)

( * ) Notice: Subject to any disclaimer, the term of this patent is extended or adjusted under 35 U.S.C. 154(b) by 0 days.

(21) Appl. No.: 16/011,458

(22) Filed: Jun. 18, 2018

(65) Prior Publication Data
US 2019/0024104 A1    Jan. 24, 2019

Related U.S. Application Data

(60) Provisional application No. 62/521,126, filed on Jun. 16, 2017.

(51) Int. Cl.
| | | |
|---|---|---|
| *C12N 15/82* | (2006.01) | |
| *A23C 11/10* | (2006.01) | |
| *C07K 14/485* | (2006.01) | |

(52) U.S. Cl.
CPC ........ *C12N 15/8257* (2013.01); *A23C 11/103* (2013.01); *C07K 14/485* (2013.01); *C12N 15/8234* (2013.01)

(58) Field of Classification Search
None
See application file for complete search history.

(56) References Cited

U.S. PATENT DOCUMENTS

| | | |
|---|---|---|
| 6,392,121 B1 | 5/2002 | Mason et al. |
| 7,723,570 B2 | 5/2010 | Piller et al. |
| 2003/0041350 A1 | 2/2003 | Kinney et al. |
| 2003/0177537 A1* | 9/2003 | Moloney .............. C07K 14/415 800/288 |
| 2003/0228612 A1 | 12/2003 | Kenward et al. |
| 2005/0193443 A1 | 9/2005 | Dale Rock et al. |

FOREIGN PATENT DOCUMENTS

| | | |
|---|---|---|
| WO | WO 1998021348 | 5/1998 |
| WO | WO2007095304 A2 | 8/2007 |
| WO | WO 2014097733 A1 | 6/2014 |

OTHER PUBLICATIONS

Vanderperre et al. Alternative protein EGF[*Homo sapiens*]. (2013) GenBank Accession CCQ43157; p. 1. (Year: 2013).*
Wong et al. The role of epidermal growth factor and its receptors in mammalian CNS. (2004) Cytokine and Growth Factor Reviews; vol. 15; pp. 147-156 (Year: 2004).*
He et al. Production of transgenic soybean seeds expressing human epidermal growth factor (hEGF) for a therapeutic formula to prevent neonatal necrotizing enterocolitis (NEC). (2015) In Vitro Cellular and Developmental Biology Animal; vol. 51; No. Suppl. 1, p. S31 (Year: 2015).*
He et al. Transgenic soybean production of bioactive human epidermal growth factor (EGF).(2016) PLOS ONE; DOI:10; 1371; pp. 1-17 (Year: 2016).*
Ding et al. High-level expression of basic fibroblast growth factor in transgenic soybean seeds and characterization of its biological activity. (2006) Biotechnol. Lett.; vol. 28; pp. 869-875 (Year: 2006).*
He et al. Transgenic Soybean Production of Bioactive Human Epidermal Growth Factor (EGF). PLOS ONE | DOI:10.1371/journal. pone.0157034 Jun. 17, 2016.
Rivin et al., Abscisic Acid and the Developmental Regulation of Embryo Storage Proteins in Maize, Plant Physiol., 1991, 95, 358-365; abstract, p. 362, col. 1, para 1, p. 363, col. 1, para 3.
Kinney et al., Cosuppression of the α subunits of β conglycinin in transgenic soybean seeds induces the formation of endoplasmic reticulum-derived protein bodies, Plant Cell, 2001, 13:1165-1178.
Schmidt et al., Silencing of soybean seed storage proteins results in a rebalanced protein composition preserving seed protein content without major collateral changes in the metabolome and transcriptome, Plant Physiology, 2011, 156: 330-345.
Herman, Soybean Seed Proteome Rebalancing, Front. Plant Sci., 2014, 5:437. doi:10.3389/fpls.2014.00437.
Schmidt et al., Transgenic soya bean seeds accumulating β-carotene exhibit the collateral enhancements of oleate and protein content traits, Plant Biotechnol. J., 2015, 13: 590-600. doi: 10.IIII/pbi. 12286. doi:10.3389/fpls.2014.00437.
Rowley et al., The upstream domain of soybean oleosin genes contains regulatory elements similar to those of legume storage proteins, Biochim. Biophys. Acta., 1997, 1345: 1-4.
Schmidt et al., The potential of engineering functional-feed soybeans for sustainable aquaculture feed, Front Plant Sci., 2016, 7: 440. Doi:10.3389/fpls.2016.00440.
Schmidt et al., Proteome rebalancing in soybean seeds can be exploited to enhance foreign protein accumulation, Plant Biotech J., 2008, 6: 832-842.

* cited by examiner

*Primary Examiner* — Cathy Kingdon Worley
(74) *Attorney, Agent, or Firm* — Nguyen Tarbet LLC

(57) ABSTRACT

Methods and compositions for producing epidermal growth factor (EGF) in soybean seeds featuring the use of transgenic soybean seeds expressing a seed-specific codon optimized gene encoding of the hEGF protein. Using these methods, the production of hEGF is sufficient and the activity of the EGF protein is comparable to commercially available EGF. The present invention shows the feasibility of using soybean seeds as a biofactory to produce therapeutic agents for a delivery platform, e.g., in a soymilk delivery platform.

5 Claims, 8 Drawing Sheets
(5 of 8 Drawing Sheet(s) Filed in Color)
Specification includes a Sequence Listing.

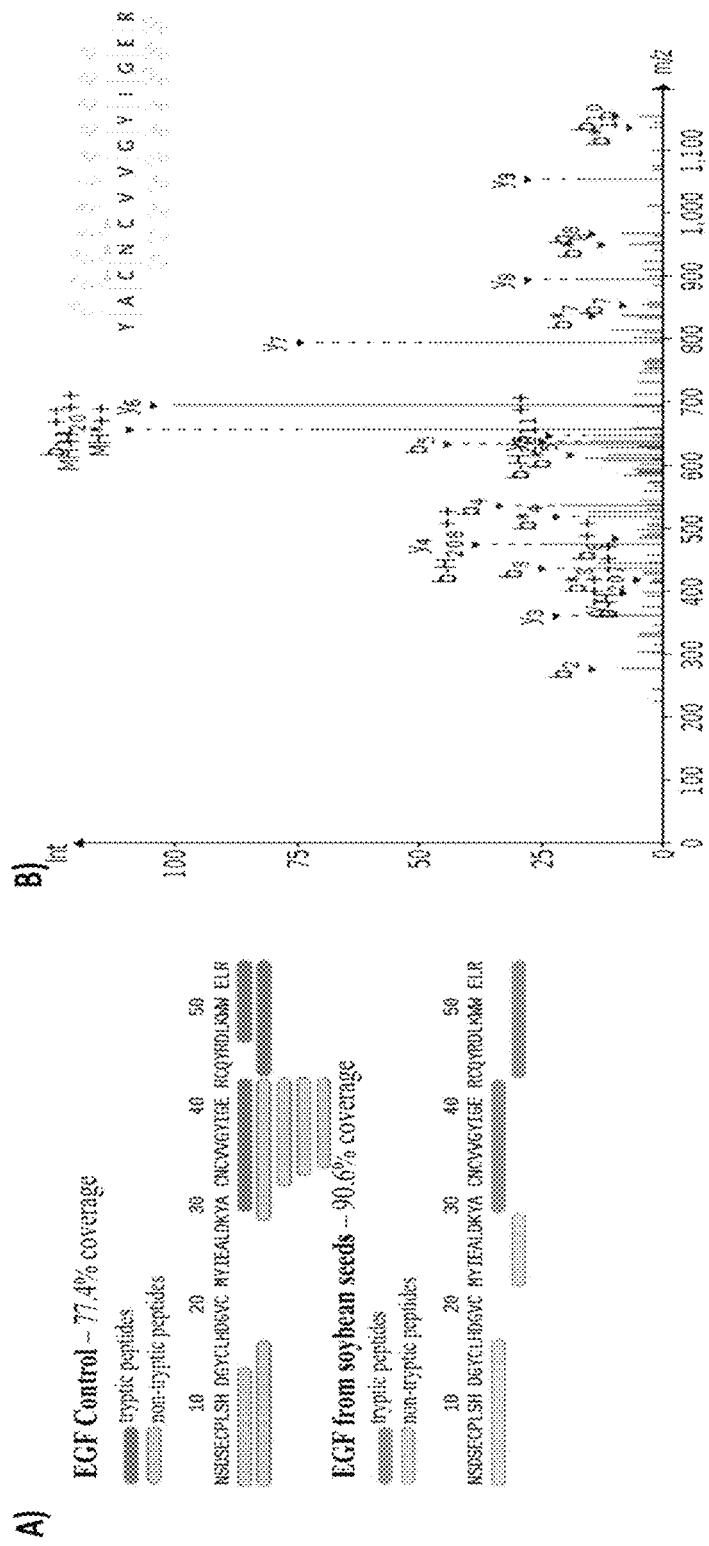

| Pathways | Biochemical Name | EGF/WTM |
|---|---|---|
| Proteinogenic Amino Acids | glycine | 1.29 |
| | alanine | 1.26 |
| | aspartate | 1.25 |
| | lysine | 1.49 |
| | methionine | 1.22 |
| | threonine | 1.19 |
| | histidine | 1.41 |
| | proline | 1.29 |
| | isoleucine | 1.55 |
| | valine | 1.38 |
| | tryptophan | 1.34 |
| | tyrosine | 0.82 |
| Aromatic Amino acid Metabolism | quinate | 1.93 |
| | shikimate | 1.65 |
| | kynurenine | 1.67 |
| | xanthurenate | 0.32 |
| Cysteine/Methionine Metabolism | s-adenosylhomocysteine (SAH) | 1.24 |
| | s-methylmethionine | 19.4 |
| | nicotianamine | 1.27 |
| From Proteolysis | Methionine sulfoxide | 1.36 |
| | Cysteine sulfinic acid | 1.8 |
| | N6,N6,N6 trimethyllysine | 1.44 |
| Lysine Metabolism | Trans 4 hydroxyproline | 4.7 |
| | homocitrulline | 0.72 |
| Energy Metabolism | 2 oxoadipate | 0.33 |
| | 2 hydroxyadipate | 0.61 |
| | sucrose | 1.26 |
| | Nicotinamide adenine dinucleotide (NAD+) | 2.47 |
| | Glucose 6 phosphate | 0.53 |
| Sugars | glucuronate | 8.24 |
| | 3 deoxyoctulosonate | 1.58 |
| | ribonate | 1.94 |
| | galactonate | 1.42 |
| | Glucarate (saccharate) | 1.72 |
| | Gulonic acid | 1.79 |
| | Mannitol/sorbitol | 1.74 |
| | galactinol | 0.55 |

Human EGF sequence

```
 91 gtaagaaatagtgactctgaatgtcccctgtcccacgatgggtac
     V  R  N  S  D  S  E  C  P  L  S  H  D  G  Y
136 tgcctccatgatggtgtgtgcatgtatattgaagcattggacaag
     C  L  H  D  G  V  C  M  Y  I  E  A  L  D  K
181 tatgcatgcaactgtgttgttggctacatcggggagcgatgtcag
     Y  A  C  N  C  V  V  G  Y  I  G  E  R  C  Q
226 taccgagacctgaagtggtgggaactgcgc 255    (SEQ ID NO: 23)
     Y  R  D  L  K  W  W  E  L  R        (SEQ ID NO: 35)
```

FIG. 7B

Optimized EGF sequence for soybean transformation

```
 46 tctctttcttcagccgaaaattccgatagtgagtgtccactctcc
     S  L  S  S  A  E  N  S  D  S  E  C  P  L  S
 91 catgatggctattgtttgcacgacggagtttgcatgtatattgaa
     H  D  G  Y  C  L  H  D  G  V  C  M  Y  I  E
136 gctttggataagtacgcatgtaactgcgttgtgggatatatcggt    (SEQ ID NO: 1)
     A  L  D  K  Y  A  C  N  C  V  V  G  Y  I  G
181 gaaagatgccaatacagggacctcaaatggtgggagctgagataa 225
     E  R  C  Q  Y  R  D  L  K  W  W  E  L  R  *    (SEQ ID NO: 12)
```

FIG. 8A

Expression cassettes were both targeted to ER so all had a 5' ER sequence (pink). The protein to encode was human EGF (blue).

→ (SEQ ID NO: 24) (pink)

MKTNLFLFLIFSLLLSLSSAEFKTNLFLFLIFSLLLSLSSAENSDSECP
LSHDGYCLHDGVCMYIEALDKYACNCVVGYIGERCQYRDLKWWE
LRSEK → (SEQ ID NO: 36) (blue)

FIG. 8B

A construct tested but not give as high expression was both targeted to the ER and retained in the ER by a KHDEL 3' sequence (pink).

→ (SEQ ID NO: 24) (pink)

MKTNLFLFLIFSLLLSLSSAEFKTNLFLFLIFSLLLSLSSAENSDSECP
LSHDGYCLHDGVCMYIEALDKYACNCVVGYIGERCQYRDLKWWE
LRSEKHDEL

→ (SEQ ID NO: 25) (pink)
(SEQ ID NO: 37)
(blue)

FIG. 8C

Nucleic Acid sequence for expression cassette: (SEQ ID NO: 38)
KHDEL (SEQ ID NO.: 25)

A nucleotide sequence (SEQ ID NO: 38) for an expression cassette. Underlined is the NOT1 restriction site for cloning purposes. The red highlighted sequence of SEQ ID NO: 38 is the ER directed 5' sequence. The green highlighted sequence of SEQ ID NO: 38 is the codon optimized nucleic acid sequence for EGF in soybean. The yellow highlighted sequence of SEQ ID NO: 38 refers to the ER retention sequence (encodes [[KDEL]] KHDEL; SEQ ID NO: [[40]] 25), which was not on all constructs. The bold nucleotides represent stop codons.

GCGGCCGCCCG
TCTGA
AAAGCATGATGAACTTTAATGAGCG GCCGC

SEQUENCE LISTING

<160> NUMBER OF SEQ ID NOS: 42

<210> SEQ ID NO 1
<211> LENGTH: 180
<212> TYPE: DNA
<213> ORGANISM: Artificial Sequence
<220> FEATURE:
<223> OTHER INFORMATION: Modified EGF DNA sequence

<400> SEQUENCE: 1

```
tctctttctt cagccgaaaa ttccgatagt gagtgtccac tctcccatga tggctattgt      60
ttgcacgacg gagtttgcat gtatattgaa gctttggata agtacgcatg taactgcgtt     120
gtgggatata tcggtgaaag atgccaatac agggacctca aatggtggga gctgagataa    180
```

<210> SEQ ID NO 2
<211> LENGTH: 171
<212> TYPE: DNA
<213> ORGANISM: Artificial Sequence
<220> FEATURE:
<223> OTHER INFORMATION: Altered mod hEGF nucleaic acid sequence

<400> SEQUENCE: 2

```
tcagccgaaa cttccgatag tgagtgtcca ctctcccatg atggctattg tttgcacgac      60
ggagttcgca tgtatattga agctttggat aagtacgcat gtaactgcgt tgtgggatat     120
atcggtgaaa gatgccaata cagggacctc aaatggtggg agctgagata a              171
```

<210> SEQ ID NO 3
<211> LENGTH: 171
<212> TYPE: DNA
<213> ORGANISM: Artificial Sequence
<220> FEATURE:
<223> OTHER INFORMATION: Altered modhEGF nucleic acid sequence

<400> SEQUENCE: 3

```
tcagccgaaa actccgctag tgagtgtcca ctctcccatg atggctattg tttgcacgac      60
ggagttcgca tgtatattga agctttggat aagtacgcat ataactgcgt tgtgggatat     120
atcggtgaaa gatgccaata cagggacctc aaatggtggg agctgagata a              171
```

<210> SEQ ID NO 4
<211> LENGTH: 171
<212> TYPE: DNA
<213> ORGANISM: Artificial Sequence
<220> FEATURE:
<223> OTHER INFORMATION: Altered ModhEGF nucleic acid sequence

<400> SEQUENCE: 4

```
tcagccgaaa actccgctag tgagtgttca ctctcccatg atggcgattg tttgcacgac      60
ggagttcgca tgtatattga agctttggat aagtacgcat ataactgcgt tgtggaatat     120
atcggtgaaa gaggccaata cagggacctc aaacggtggg agctgagata a              171
```

<210> SEQ ID NO 5
<211> LENGTH: 171
<212> TYPE: DNA
<213> ORGANISM: Artificial Sequence
<220> FEATURE:
<223> OTHER INFORMATION: Altered modhEGF nucleic acid sequence

<400> SEQUENCE: 5

```
tcagccgaaa actccgctat tgagtgttca ctctccctg atggcgattg tttgcacgac       60
ggagttcgca tgtatattga agctttgtat aagtacgcat ataactgcgt tgtggaatat     120
```
atcggtgaaa gaggccaata caggaacctc aaacggtggg agctgagata a            171

<210> SEQ ID NO 6
<211> LENGTH: 171
<212> TYPE: DNA
<213> ORGANISM: Artificial Sequence
<220> FEATURE:
<223> OTHER INFORMATION: Altered modhEGF nucleic acid sequence

<400> SEQUENCE: 6
tcagccgaaa actccgctat tgagtgttca ctctcccctg atggcgattg tttgcaagac     60
gtagttcgca tgtatagtga agctttgtat aagtacgcat ataactgcgt tgtggaatat    120
ctcggtgaaa gaggccaata caggaacctc aaacggtgga agctgagata a            171

<210> SEQ ID NO 7
<211> LENGTH: 171
<212> TYPE: DNA
<213> ORGANISM: Artificial Sequence
<220> FEATURE:
<223> OTHER INFORMATION: Altered modhEGF nucleic acid sequence

<400> SEQUENCE: 7
tcagccgaaa atcccgatag tgagtgtcca ctctgccatg ctggctattg ttcgcacgac     60
ggagtttgca tgtatattgt agctgtggat aagtacgcat gtaactgcgc tgtgggatat    120
atcggtgcaa gatgccaata cagcgacctc aaatggtggg acccgagata a            171

<210> SEQ ID NO 8
<211> LENGTH: 171
<212> TYPE: DNA
<213> ORGANISM: Artificial Sequence
<220> FEATURE:
<223> OTHER INFORMATION: Altered modhEGF nucleic acid sequence

<400> SEQUENCE: 8
tcagccgaaa atcccgatcg tgagtgtcca ctctgccatg ctggctattg ttcgcacgac     60
ggagtttgca tgtatattgt agctgtggat aagtacgcat gtaactgcgc tgtgggatat    120
atcggtgcaa gatgccaata cagcgacctc aaatggtggg acccgagata a            171

<210> SEQ ID NO 9
<211> LENGTH: 171
<212> TYPE: DNA
<213> ORGANISM: Artificial Sequence
<220> FEATURE:
<223> OTHER INFORMATION: Altered modhEGF nucleic acid sequence

<400> SEQUENCE: 9
tcagccgaaa atcccgatcg tgagtgtcca ctctgccatg ctggctattg ttcgcacgac     60
ggagtttgca tgtatattgt agctgtggat aagtacgcat gtaactgcgc tgtgggatat    120
atcggtgcaa gatgccaata cagcgacctc aaatggtggg acccgagata a            171

<210> SEQ ID NO 10
<211> LENGTH: 171
<212> TYPE: DNA
<213> ORGANISM: Artificial Sequence
<220> FEATURE:
<223> OTHER INFORMATION: Altered modhEGF nucleic acid sequence

<400> SEQUENCE: 10
tcagccgaaa atcccgatcg tgcgtgtcca ctctgccatg ctgtctattg ttcgcacgac     60

```
ggagtttgca tgtatattgt agctgtggat aagtacgcat gtaactgcgc tgtgggatat    120
atcggtgcaa gatgccaata cagcgacctc aaatggtggg acccgagata a             171
```

<210> SEQ ID NO 11
<211> LENGTH: 171
<212> TYPE: DNA
<213> ORGANISM: Artificial Sequence
<220> FEATURE:
<223> OTHER INFORMATION: Altered modhEGF nucleic acid sequence

<400> SEQUENCE: 11

```
tcagccgaaa atcccgatcg tgcgtgtcta ctctgccatg ctgtctattg ttcgcacgac    60
agagtttgca tgtatattgt agctgtggat aagtactcat gtaactgcgc tgtgggatgt   120
atcggtgcaa gatgccaata cagcgacctc aattggtggg agccgagata a             171
```

<210> SEQ ID NO 12
<211> LENGTH: 59
<212> TYPE: PRT
<213> ORGANISM: Artificial Sequence
<220> FEATURE:
<223> OTHER INFORMATION: Modified EGF protein sequence

<400> SEQUENCE: 12

```
Ser Leu Ser Ser Ala Glu Asn Ser Asp Ser Glu Cys Pro Leu Ser His
1               5                   10                  15

Asp Gly Tyr Cys Leu His Asp Gly Val Cys Met Tyr Ile Glu Ala Leu
            20                  25                  30

Asp Lys Tyr Ala Cys Asn Cys Val Val Gly Tyr Ile Gly Glu Arg Cys
        35                  40                  45

Gln Tyr Arg Asp Leu Lys Trp Trp Glu Leu Arg
    50                  55
```

<210> SEQ ID NO 13
<211> LENGTH: 59
<212> TYPE: PRT
<213> ORGANISM: Artificial Sequence
<220> FEATURE:
<223> OTHER INFORMATION: Altered modhEGF protein sequence

<400> SEQUENCE: 13

```
Ser Leu Ser Ser Ala Glu Thr Ser Asp Ser Glu Cys Pro Leu Ser His
1               5                   10                  15

Asp Gly Tyr Cys Leu His Asp Gly Val Arg Met Tyr Ile Glu Ala Leu
            20                  25                  30

Asp Lys Tyr Ala Cys Asn Cys Val Val Gly Tyr Ile Gly Glu Arg Cys
        35                  40                  45

Gln Tyr Arg Asp Leu Lys Trp Trp Glu Leu Arg
    50                  55
```

<210> SEQ ID NO 14
<211> LENGTH: 59
<212> TYPE: PRT
<213> ORGANISM: Artificial Sequence
<220> FEATURE:
<223> OTHER INFORMATION: Altered modhEGF protein sequence

<400> SEQUENCE: 14

```
Ser Leu Ser Ser Ala Glu Thr Ser Ala Ser Glu Cys Pro Leu Ser His
1               5                   10                  15

Asp Gly Tyr Cys Leu His Asp Gly Val Arg Met Tyr Ile Glu Ala Leu
            20                  25                  30
```

Asp Lys Tyr Ala Tyr Asn Cys Val Val Gly Tyr Ile Gly Glu Arg Cys
            35                  40                  45

Gln Tyr Arg Asp Leu Lys Trp Trp Glu Leu Arg
        50                  55

<210> SEQ ID NO 15
<211> LENGTH: 59
<212> TYPE: PRT
<213> ORGANISM: Artificial Sequence
<220> FEATURE:
<223> OTHER INFORMATION: Altered modhEGF protein sequence

<400> SEQUENCE: 15

Ser Leu Ser Ser Ala Glu Thr Ser Ala Ser Glu Cys Ser Leu Ser His
1               5                   10                  15

Asp Gly Asp Cys Leu His Asp Gly Val Arg Met Tyr Ile Glu Ala Leu
            20                  25                  30

Asp Lys Tyr Ala Tyr Asn Cys Val Val Glu Tyr Ile Gly Glu Arg Gly
            35                  40                  45

Gln Tyr Arg Asp Leu Lys Arg Trp Glu Leu Arg
        50                  55

<210> SEQ ID NO 16
<211> LENGTH: 59
<212> TYPE: PRT
<213> ORGANISM: Artificial Sequence
<220> FEATURE:
<223> OTHER INFORMATION: Altered modhEGF protein sequence

<400> SEQUENCE: 16

Ser Leu Ser Ser Ala Glu Thr Ser Ala Ile Glu Cys Ser Leu Ser Pro
1               5                   10                  15

Asp Gly Asp Cys Leu His Asp Gly Val Arg Met Tyr Ile Glu Ala Leu
            20                  25                  30

Tyr Lys Tyr Ala Tyr Asn Cys Val Val Glu Tyr Ile Gly Glu Arg Gly
            35                  40                  45

Gln Tyr Arg Asn Leu Lys Arg Trp Glu Leu Arg
        50                  55

<210> SEQ ID NO 17
<211> LENGTH: 59
<212> TYPE: PRT
<213> ORGANISM: Artificial Sequence
<220> FEATURE:
<223> OTHER INFORMATION: Altered modhEGF protein sequence

<400> SEQUENCE: 17

Ser Leu Ser Ser Ala Glu Thr Ser Ala Ile Glu Cys Ser Leu Ser Pro
1               5                   10                  15

Asp Gly Asp Cys Leu Gln Asp Val Val Arg Met Tyr Ser Glu Ala Leu
            20                  25                  30

Tyr Lys Tyr Ala Tyr Asn Cys Val Val Glu Tyr Leu Gly Glu Arg Gly
            35                  40                  45

Gln Tyr Arg Asn Leu Lys Arg Trp Lys Leu Arg
        50                  55

<210> SEQ ID NO 18
<211> LENGTH: 59
<212> TYPE: PRT
<213> ORGANISM: Artificial Sequence
<220> FEATURE:

<223> OTHER INFORMATION: Altered modhEGF protein sequence

<400> SEQUENCE: 18

Ser Leu Ser Ser Ala Glu Asn Ala Asp Ser Glu Cys Pro Leu Ser His
1               5                   10                  15

Asp Gly Tyr Cys Leu His Asp Gly Val Cys Met Tyr Ile Val Ala Leu
            20                  25                  30

Asp Lys Tyr Ala Cys Asn Cys Val Val Gly Tyr Ile Gly Glu Arg Cys
        35                  40                  45

Gln Tyr Arg Asp Leu Lys Trp Trp Glu Leu Arg
    50                  55

<210> SEQ ID NO 19
<211> LENGTH: 59
<212> TYPE: PRT
<213> ORGANISM: Artificial Sequence
<220> FEATURE:
<223> OTHER INFORMATION: Altered modhEGF protein sequence

<400> SEQUENCE: 19

Ser Leu Ser Ser Ala Glu Asn Ala Asp Arg Glu Cys Pro Leu Ser His
1               5                   10                  15

Ala Gly Tyr Cys Leu His Asp Gly Val Cys Met Tyr Ile Val Ala Leu
            20                  25                  30

Asp Lys Tyr Ala Cys Asn Cys Val Val Gly Tyr Ile Gly Glu Arg Cys
        35                  40                  45

Gln Tyr Arg Asp Leu Lys Trp Trp Glu Leu Arg
    50                  55

<210> SEQ ID NO 20
<211> LENGTH: 59
<212> TYPE: PRT
<213> ORGANISM: Artificial Sequence
<220> FEATURE:
<223> OTHER INFORMATION: Altered modhEGF protein sequence

<400> SEQUENCE: 20

Ser Leu Ser Ser Ala Glu Asn Ala Asp Arg Glu Cys Pro Leu Cys His
1               5                   10                  15

Ala Gly Tyr Cys Ser His Asp Gly Val Cys Met Tyr Ile Val Ala Leu
            20                  25                  30

Asp Lys Tyr Ala Cys Asn Cys Ala Val Gly Tyr Ile Gly Glu Arg Cys
        35                  40                  45

Gln Tyr Ser Asp Leu Lys Trp Trp Glu Pro Arg
    50                  55

<210> SEQ ID NO 21
<211> LENGTH: 59
<212> TYPE: PRT
<213> ORGANISM: Artificial Sequence
<220> FEATURE:
<223> OTHER INFORMATION: Altered modhEGF protein sequence

<400> SEQUENCE: 21

Ser Leu Ser Ser Ala Glu Asn Ala Asp Arg Ala Cys Pro Leu Cys His
1               5                   10                  15

Ala Val Tyr Cys Ser His Asp Gly Val Cys Met Tyr Ile Val Ala Val
            20                  25                  30

Asp Lys Tyr Ala Cys Asn Cys Ala Val Gly Tyr Ile Gly Ala Arg Cys
        35                  40                  45

```
Gln Tyr Ser Asp Leu Lys Trp Trp Glu Pro Arg
    50                  55
```

<210> SEQ ID NO 22
<211> LENGTH: 59
<212> TYPE: PRT
<213> ORGANISM: Artificial Sequence
<220> FEATURE:
<223> OTHER INFORMATION: Altered modhEGF protein sequence

<400> SEQUENCE: 22

```
Ser Leu Ser Ser Ala Glu Asn Ala Asp Arg Ala Cys Leu Leu Cys His
1               5                   10                  15

Ala Val Tyr Cys Ser His Asp Arg Val Cys Met Tyr Ile Val Ala Val
            20                  25                  30

Asp Lys Tyr Ser Cys Asn Cys Ala Val Gly Cys Ile Gly Ala Arg Cys
        35                  40                  45

Gln Tyr Ser Asp Leu Asn Trp Trp Glu Pro Arg
    50                  55
```

<210> SEQ ID NO 23
<211> LENGTH: 165
<212> TYPE: DNA
<213> ORGANISM: Homo sapiens

<400> SEQUENCE: 23

```
gtaagaaata gtgactctga atgtccctg tcccacgatg ggtactgcct ccatgatggt    60
gtgtgcatgt atattgaagc attggacaag tatgcatgca actgtgttgt tggctacatc   120
ggggagcgat gtcagtaccg agacctgaag tggtgggaac tgcgc                  165
```

<210> SEQ ID NO 24
<211> LENGTH: 39
<212> TYPE: PRT
<213> ORGANISM: Homo sapiens

<400> SEQUENCE: 24

```
Met Lys Thr Asn Leu Phe Leu Phe Leu Ile Phe Ser Leu Leu Leu Ser
1               5                   10                  15

Leu Ser Ser Ala Glu Phe Lys Thr Asn Leu Phe Leu Phe Leu Ile Phe
            20                  25                  30

Ser Leu Leu Leu Ser Leu Ser
        35
```

<210> SEQ ID NO 25
<211> LENGTH: 5
<212> TYPE: PRT
<213> ORGANISM: Homo sapiens

<400> SEQUENCE: 25

```
Lys His Asp Glu Leu
1               5
```

<210> SEQ ID NO 26
<211> LENGTH: 162
<212> TYPE: DNA
<213> ORGANISM: Artificial Sequence
<220> FEATURE:
<223> OTHER INFORMATION: Modified hEGF coding region

<400> SEQUENCE: 26

```
aattccgata gtgagtgtcc actctcccat gatggctatt gtttgcacga cggagtttgc    60
```

```
atgtatattg aagctttgga taagtacgca tgtaactgcg ttgtgggata tatcggtgaa    120
agatgccaat acagggacct caaatggtgg gagctgagat aa                      162
```

<210> SEQ ID NO 27
<211> LENGTH: 162
<212> TYPE: DNA
<213> ORGANISM: Artificial Sequence
<220> FEATURE:
<223> OTHER INFORMATION: Altered modhEGF coding nucleic acid sequence

<400> SEQUENCE: 27

```
acttccgata gtgagtgtcc actctcccat gatggctatt gtttgcacga cggagttcgc    60
atgtatattg aagctttgga taagtacgca tgtaactgcg ttgtgggata tatcggtgaa    120
agatgccaat acagggacct caaatggtgg gagctgagat aa                      162
```

<210> SEQ ID NO 28
<211> LENGTH: 162
<212> TYPE: DNA
<213> ORGANISM: Artificial Sequence
<220> FEATURE:
<223> OTHER INFORMATION: Altered modhEGF coding nucleic acid sequence

<400> SEQUENCE: 28

```
aactccgcta gtgagtgtcc actctcccat gatggctatt gtttgcacga cggagttcgc    60
atgtatattg aagctttgga taagtacgca tataactgcg ttgtgggata tatcggtgaa    120
agatgccaat acagggacct caaatggtgg gagctgagat aa                      162
```

<210> SEQ ID NO 29
<211> LENGTH: 162
<212> TYPE: DNA
<213> ORGANISM: Artificial Sequence
<220> FEATURE:
<223> OTHER INFORMATION: Altered modhEGF coding nucleic acid sequence

<400> SEQUENCE: 29

```
aactccgcta gtgagtgttc actctcccat gatggcgatt gtttgcacga cggagttcgc    60
atgtatattg aagctttgga taagtacgca tataactgcg ttgtggaata tatcggtgaa    120
agaggccaat acagggacct caaacggtgg gagctgagat aa                      162
```

<210> SEQ ID NO 30
<211> LENGTH: 162
<212> TYPE: DNA
<213> ORGANISM: Artificial Sequence
<220> FEATURE:
<223> OTHER INFORMATION: Altered modhEGF cding nucleic acid sequence

<400> SEQUENCE: 30

```
aactccgcta ttgagtgttc actctcccct gatggcgatt gtttgcacga cggagttcgc    60
atgtatattg aagctttgta taagtacgca tataactgcg ttgtggaata tatcggtgaa    120
agaggccaat acaggaacct caaacggtgg gagctgagat aa                      162
```

<210> SEQ ID NO 31
<211> LENGTH: 162
<212> TYPE: DNA
<213> ORGANISM: Artificial Sequence
<220> FEATURE:
<223> OTHER INFORMATION: Altered modhEGF coding nucleic acid sequence

<400> SEQUENCE: 31

```
aactccgcta ttgagtgttc actctcccct gatggcgatt gtttgcaaga cgtagttcgc    60
```

```
atgtatagtg aagctttgta taagtacgca tataactgcg ttgtggaata tctcggtgaa    120
agaggccaat acaggaacct caaacggtgg aagctgagat aa                       162
```

<210> SEQ ID NO 32
<211> LENGTH: 18
<212> TYPE: DNA
<213> ORGANISM: Homo sapiens

<400> SEQUENCE: 32

```
tctctttctt cagccgaa                                                   18
```

<210> SEQ ID NO 33
<211> LENGTH: 18
<212> TYPE: DNA
<213> ORGANISM: Artificial Sequence
<220> FEATURE:
<223> OTHER INFORMATION: Altered nucleic acid sequence

<400> SEQUENCE: 33

```
tcttttctt cagccgaa                                                    18
```

<210> SEQ ID NO 34
<211> LENGTH: 18
<212> TYPE: DNA
<213> ORGANISM: Artificial Sequence
<220> FEATURE:
<223> OTHER INFORMATION: Altered nucleic acid sequence

<400> SEQUENCE: 34

```
tcttttctt aagccgaa                                                    18
```

<210> SEQ ID NO 35
<211> LENGTH: 54
<212> TYPE: PRT
<213> ORGANISM: Homo sapiens

<400> SEQUENCE: 35

```
Val Arg Ser Asp Ser Glu Cys Pro Leu Ser His Asp Gly Tyr Cys Leu
1               5                   10                  15

His Asp Gly Val Cys Met Tyr Ile Glu Ala Leu Asp Lys Tyr Ala Cys
            20                  25                  30

Asn Cys Val Val Gly Tyr Ile Gly Glu Arg Cys Gln Tyr Arg Asp Leu
        35                  40                  45

Lys Trp Trp Glu Leu Arg
    50
```

<210> SEQ ID NO 36
<211> LENGTH: 59
<212> TYPE: PRT
<213> ORGANISM: Artificial Sequence
<220> FEATURE:
<223> OTHER INFORMATION: Synthetic Human EGF Protein_construct 1

<400> SEQUENCE: 36

```
Ser Ala Glu Asn Ser Asp Ser Glu Cys Pro Leu Ser His Asp Gly Tyr
1               5                   10                  15

Cys Leu His Asp Gly Val Cys Met Tyr Ile Glu Ala Leu Asp Lys Tyr
            20                  25                  30

Ala Cys Asn Cys Val Val Gly Tyr Ile Gly Glu Arg Cys Gln Tyr Arg
        35                  40                  45

Asp Leu Lys Trp Trp Glu Leu Arg Ser Glu Lys
    50                  55
```

<210> SEQ ID NO 37
<211> LENGTH: 63
<212> TYPE: PRT
<213> ORGANISM: Artificial Sequence
<220> FEATURE:
<223> OTHER INFORMATION: Synthetic human EGF protein_ cassette 2

<400> SEQUENCE: 37

Ser Ala Glu Asn Ser Asp Ser Glu Cys Pro Leu Ser His Asp Gly Tyr
1               5                   10                  15

Cys Leu His Asp Gly Val Cys Met Tyr Ile Glu Ala Leu Asp Lys Tyr
            20                  25                  30

Ala Cys Asn Cys Val Val Gly Tyr Ile Gly Glu Arg Cys Gln Tyr Arg
        35                  40                  45

Asp Leu Lys Trp Trp Glu Leu Arg Ser Glu Lys His Asp Glu Leu
    50                  55                  60

<210> SEQ ID NO 38
<211> LENGTH: 331
<212> TYPE: DNA
<213> ORGANISM: Artificial Sequence
<220> FEATURE:
<223> OTHER INFORMATION: Synthetic_Full Cassette

<400> SEQUENCE: 38
gcggccgccc gatgaagact aatctttttc tctttctcat cttttcactt ctcctatcat    60
tatcctcggc cgaattcaag actaacctgt ttcttttctt gattttttagc cttttgctct   120 ctctttcttc agccgaaaat ccgatagtg agtgtccact ctcccatgat ggctattgtt    180
tgcacgacgg agtttgcatg tatattgaag ctttggataa gtacgcatgt aactgcgttg   240
tgggatatat cggtgaaaga tgccaataca gggacctcaa atggtgggag ctgagatctg   300
aaaagcatga tgaactttaa tgagcggccg c                                  331

<210> SEQ ID NO 39
<211> LENGTH: 11
<212> TYPE: PRT
<213> ORGANISM: Artificial Sequence
<220> FEATURE:
<223> OTHER INFORMATION: Synthetic Low MW protein

<400> SEQUENCE: 39

Cys Asn Cys Val Val Gly Tyr Ile Gly Glu Arg
1               5                   10

<210> SEQ ID NO 40
<211> LENGTH: 20
<212> TYPE: DNA
<213> ORGANISM: Artificial Sequence
<220> FEATURE:
<223> OTHER INFORMATION: glycinin promoter primer

<400> SEQUENCE: 40
tcattcacct tcctctcttc                                               20

<210> SEQ ID NO 41
<211> LENGTH: 20
<212> TYPE: DNA
<213> ORGANISM: Artificial Sequence
<220> FEATURE:
<223> OTHER INFORMATION: primer specific to HygF

<400> SEQUENCE: 41

```
ctcactattc ctttgccctc                                               20

<210> SEQ ID NO 42
<211> LENGTH: 20
<212> TYPE: DNA
<213> ORGANISM: Artificial Sequence
<220> FEATURE:
<223> OTHER INFORMATION: specific primer to HygR

<400> SEQUENCE: 42
ctgacctatt gcatctcccg                                               20
```

METHODS AND COMPOSITIONS FOR PRODUCING EPIDERMAL GROWTH FACTOR (EGF) IN SOYBEANS

CROSS REFERENCE

This application claims priority to U.S. Provisional Patent Application No. 62/521,126 filed Jun. 16, 2017, the specification(s) of which is/are incorporated herein in their entirety by reference.

GOVERNMENT SUPPORT

This invention was made with government support under Grant No. R21 DK094065 awarded by NIH. The government has certain rights in the invention.

REFERENCE TO SEQUENCE LISTING

Applicant asserts that the paper copy of the Sequence Listing is identical to the Sequence Listing in computer readable form found on the accompanying computer file, entitled UNIA 17.29_NP_Sequence_Listing_ST25.txt._The content of the sequence listing is incorporated herein by reference in its entirety.

FIELD OF THE INVENTION

The present invention relates to protein production in plants, more particularly to production of human epidermal growth factor (hEGF) in soybeans and methods of treating conditions or symptoms of conditions using hEGF in solution.

BACKGROUND OF THE INVENTION

Necrotizing enterocolitis (NEC) is a condition of premature infants that results from the gut microbiome invading immature intestinal tissues. This results in a life-threatening disease that is frequently treated with the surgical removal of diseases and dead tissues. Epidermal growth factor (EGF), typically found in bodily fluids such as amniotic fluid, saliva, and breast milk, is an intestinal trophic growth factor and may reduce the onset of NEC in premature infants. It has been demonstrated in several animal models of NEC that administration of exogenous EGF has been shown to significantly reduce the severity of intestinal injury. The proactive treatment of infants at NEC risk with EGF supplementation could therefore accelerate intestinal maturation, thus preventing the development of NEC.

The present invention features methods and compositions for producing EGF (e.g., human EGF) in soybean seeds using an optimized EGF nucleic acid sequence for soybean transformation. The production of hEGF is to levels that are biologically relevant and to activity that is comparable to commercially available EGF. Briefly, the present invention utilizes transgenic soybean seeds expressing a seed-specific codon optimized gene encoding the hEGF protein with an added ER signal tag at the N terminal (ShEGF). Expression of ShEGF regulated by the soybean seed storage protein promoter resulted in the accumulation of hEGF at >100 µg/gm of dry soybean seed. Without wishing to limit the present invention to any theory or mechanism, it is believed that 100 µg/gm of dry soybean seed is a level several fold over the estimated therapeutic requirements of 50 µg/kg weight of treated individual. The present invention shows the feasibility of using soybean seeds as a biofactory to produce therapeutic agents for a delivery platform, e.g., in a soymilk delivery platform, an infant formula, etc.

Without wishing to limit the present invention to any theory or mechanism, it is believed that the soybean-derived EGF can be used for a variety of purposes including but not limited to a sealant for intestinal walls, a cosmetic agent, a healing agent for wounds, and a treatment for diabetic skin ulcers.

SUMMARY OF THE INVENTION

The present invention features methods and compositions for producing epidermal growth factor (EGF) (e.g., human EGF; hEGF) in soybean seeds. For example, the present invention features a method of producing hEGF. The method may comprise expressing a protein encoded by SEQ ID NO: 1 (a codon-optimized gene for EGF expression) in a transgenic soybean comprising a transgene according to SEQ ID NO: 1 (see FIG. 7 for SEQ ID NO: 1). In some embodiments, the method further comprises purifying said hEGF and/or reconstituting said hEGF in a solution. In some embodiments, the solution comprises soymilk.

As such, the present invention also features a nucleic acid according to SEQ ID NO: 1. The present invention also features a protein encoded by a nucleic acid according to SEQ ID NO: 1. The present invention also features a transgenic soybean expressing SEQ ID NO: 1. The present invention also features a soymilk composition comprising soybean-derived hEGF.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

This patent application contains at least one drawing executed in color. Copies of this patent or patent application publication with color drawing(s) will be provided by the Office upon request and payment of the necessary fee. The features and advantages of the present invention will become apparent from a consideration of the following detailed description presented in connection with the accompanying drawings in which:

FIG. 4A-4B show mass spectroscopy data to detect the presence of EGF peptides in transgenic EGF soybean seeds. FIG. 4A shows a coverage of peptides detected in both commercially available EGF (green) and from transgenic soybean seeds (orange) using both trypsin (solid) and non-trypsin peptides (hatched). FIG. 4B shows raw spectra data depicting the amino acid sequence CNCVVGYIGER (SEQ ID NO: 39) detected from a low molecular weight enriched soluble dry seed protein extract from EGF transgenic soybean.

FIG. 5A shows soybean produced hEGF induces a rapid phosphorylation of Hela cell EGFR. Serum free media (SF) and SF media with soymilk alone does not induce EGFR phosphorylation and degradation. Soymilk from seeds producing ShEGF added at different concentrations (0.1, 0.05, 0.025 µg/ml) induced concentration-dependent EGFR degradation comparable to the effect of rhEGF. Serum free media and serum free media with non-transgenic soybean soymilk (negative controls) showed no effect on inducing pEGFR. In contrast soymilk from ShEGF soybeans given at different concentrations (0.1, 0.05, 0.025 µg/ml) induced pEGFR comparable to control rhEGF. pAKT indicates the functional activation of EGFR. Lamin B1 was used as a loading control. FIG. 5B shows exogenous commercial rhEGF and ShEGF induces an internalization and degradation of EGFR in Hela cells shown as a decrease in abundance assayed by immunoblot. The results shown demonstrate that soymilk alone has no intrinsic bioactivity with respect to EGFR abundance. The rhEGF is not degraded in soymilk over 24 hours having the same bioactivity as control recombinant rhEGF. Ctrl-SF media alone. Soy EGF and rhEGF are at 0.1 µg/ml. Lamin B1 was used as a loading control. FIG. 5C shows an immunohistochemical assay of Hela cells showing that ShEGF induces internalization of the EGFR comparable to that from control rhEGF. In C, the cells were first treated with soy/EGF or hEGF for 6 hours, fixed and then immunostained with EGFR antibody overnight. EGFR shows red staining while nucleus was stained by DAR and shows blue staining.

FIG. 6 shows differences (insignificant differences) between non-transgenic soybean seeds and the ShEGF transgenic seeds.

FIG. 7A shows the hEGF nucleic acid sequence (SEQ ID NO: 23) and the respective amino acid sequence (SEQ ID NO: 35). FIG. 7B shows the optimized EGF nucleic acid sequence for soybean transformation (SEQ ID NO: 1) and the respective amino acid sequence (SEQ ID NO: 12).

FIG. 8A shows an expression cassette targeted to the ER and having the 5' ER sequence (amino acid; pink) (SEQ ID NO: 24). The sequence highlighted in blue is the respective amino acid sequence (SEQ ID NO: 36).

FIG. 8B shows a construct with the ER sequence (SEQ ID NO: 24, pink), the respective amino acid sequence (SEQ ID NO: 37, blue), and the KHDEL sequence (pink, SEQ ID NO: 25).

FIG. 8C shows a nucleotide sequence (SEQ ID NO: 38) for an expression cassette. Underlined is the NOT1 restriction site for cloning purposes. The red highlighted sequence of SEQ ID NO: 38 is the ER directed 5' sequence. The green highlighted sequence of SEQ ID NO: 38 is the codon optimized nucleic acid sequence for EGF in soybean. The yellow highlighted sequence of SEQ ID NO: 38 refers to the ER retention sequence (encodes KHDEL; SEQ ID NO: 25), which was not on all constructs. Bold nucleotides represent stop codons.

DETAILED DESCRIPTION OF THE INVENTION

Referring now to FIG. 1-8, the present invention features methods and compositions for producing epidermal growth factor (EGF) (e.g., human EGF) in soybean seeds. For example, the present invention features methods for producing EGF in soybeans seeds, as well as introducing transgenes into soybeans to produce EGF, transgenic soybeans engineered to produce EGF, and soymilk compositions comprising soybean-derived EGF.

The present invention shows the accumulation of hEGF in genetically engineered soybean seeds. Further, the present invention shows that the recombinant EGF is indistinguishable from authentic hEGF and is bioactive at stimulating EGF receptor (EGFR) activity. Briefly, the present invention utilizes transgenic soybean seeds expressing a seed-specific codon optimized gene encoding of the hEGF protein with an added ER signal tag at the N terminal. Seven independent lines were grown to homozygous and found to accumulate a range of 6.7+/−3.1 to 129.0+/−36.7 ug EGF/g of dry soybean seed. Proteomic and immunoblot analysis indicate that the inserted EGF is the same as the hEGF protein. Phosphorylation and immunohistochemical assays on the EGF receptor in HeLa cells indicate the EGF protein produced in soybean seed is bioactive and comparable to commercially available hEGF.

Figure 1A:
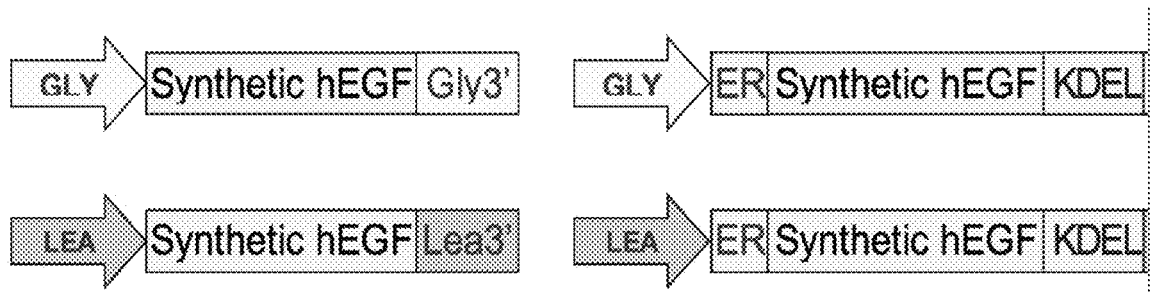
FIG. 1A shows a schematic diagram of seed-specific gene expression cassettes, e.g., to direct ShEGF. For example, synthetically produced codon-optimized hEGF gene with an ER signal added to the amino-terminus driven by glycinin regulatory elements was transformed via biolistics into somatic soybean embryos. GLY refers to the glycinin promoter. LEA refers to late embryonic abundant protein promoter. The presence of ER signal peptide/retention tag may enhance the yield of EGF accumulated in the soybean seeds.
Figure 1B:
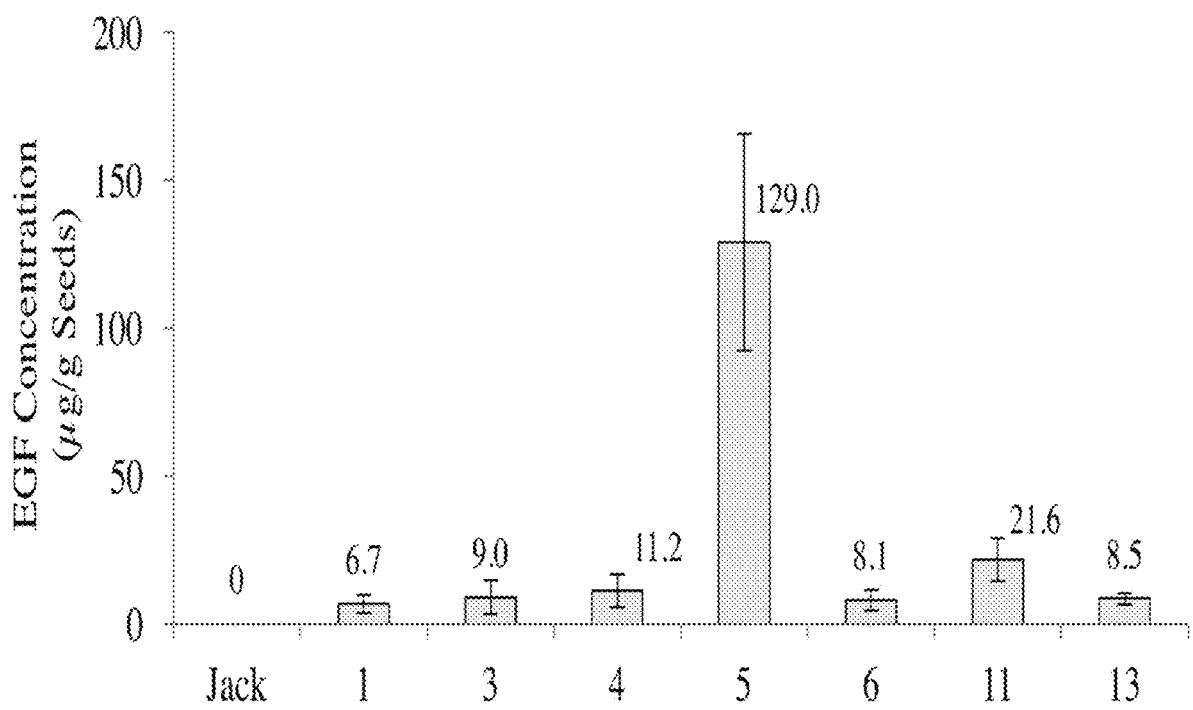
FIG. 1B shows ELISA quantification for both the detection and amount of hEGF in total soluble dry seed protein extract from 7 ShEGF transgenic soybean lines. Independent homozygous lines, 1, 3, 4, 5, 6, 11, 13 were detected to contain hEGF up to 129 µg EGF/g seed compared to undetectable amounts in non-transgenic control (Wt). Values shown are mean+/−standard error (n=3).
Figure 2:
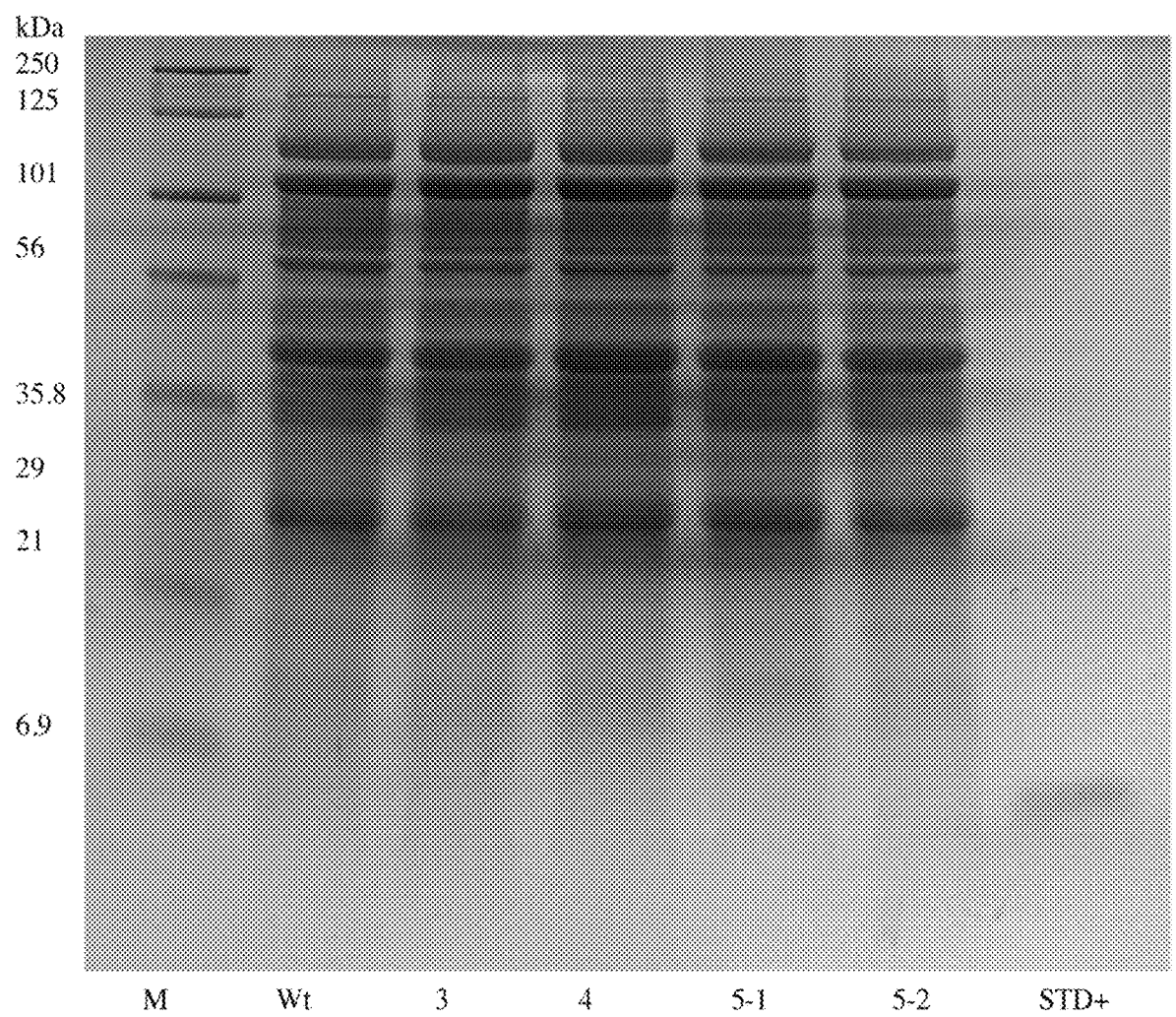
FIG. 2 shows an analysis of total soluble protein by one-dimensional gel electrophoresis of hEGF expressing transgenic soybean seeds. Proteins from 3 independent homozygous EGF transgenic soybean lines (3, 4, 5) were extracted and compared to seed extracts from non-transgenic (Wt) and commercially available hEGF standard (STD+). M marker, kDa kilobases.
Figure 3:
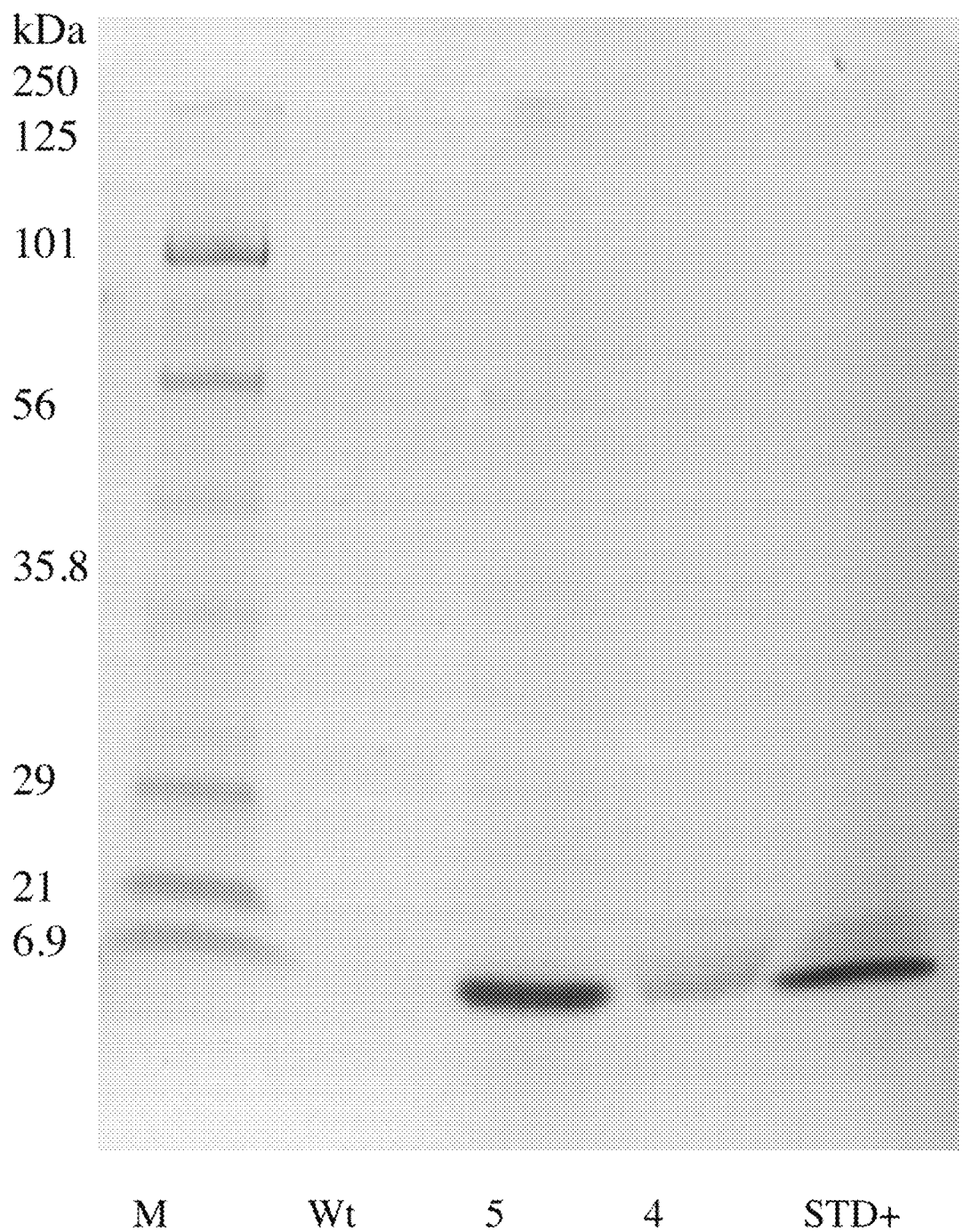
FIG. 3 shows an immunoblot of enriched small molecular weight soluble protein extracted from dry transgenic ShEGF soybean seeds. Protein extracts from two independent homozygous lines (5 and 4) are compared to both non-transgenic (Wt) and commercially available EGF standard (STD+). EGF was detected using an EGF specific antibody and indirect secondary antibody coupled to alkaline phosphatase. M marker; kDa kilodalton.

To produce hEGF in soybean, a strong soybean seed-specific promoter and terminator was used to regulate gene expression of a synthetic soybean codon optimized hEGF (ShEGF) gene that included an N-terminal 126 nucleotide ER-signal sequence (FIG. 1A). In the engineering strategy for the hEGF expression in soybean, the components of the prepro portions of hEGF were eliminated in preference to produce only the final recombinant hEGF product. To facilitate the co-translational transfer of the EGF into the ER lumen for disulfide bond formation a plant signal sequence was added so that the hEGF synthesized would be as a pre-hEGF. The Gly::ShEGF construct was used for biolistic transformation of soybean somatic embryo cells as outlined in Schmidt M A, Herman E M, Plant Biotechnol J. 2008; 6: 832-842; Schmidt M A, Herman E M, Mol Plant. 2008; 1: 910-924; Schmidt M A, Parrott W A, Hildebrand D F, Berg R H, Cooksey A, Pendarvis K, et al., Plant Biotechnol J. 2015; 13: 590-600; and Schmidt M A, Tucker D M, Cahoon E B, Parrott W A. Plant Cell Rep. 2004; 24: 383-391. Embryos were selected in liquid culture by hygromycin B and individual regenerated lines were separated, propagated, and induced to form cotyledonary embryos. The cotyledonary embryos were evaluated for hEGF production using EGF-specific ELISA that indicated a variation of heterologous protein production. The most promising EGF expressing lines were moved forward for regeneration by desiccating and subsequent germination. The initial T0 generation EGF transgenic plants were grown in the greenhouse and further selected by genomic PCR for an additional 2-3 generations. Additionally, each generation of seeds produced by the selected lines were assayed for hEGF content by ELISA. The hEGF content of each line in seeds representative of the homozygous population is shown in FIG. 1B. The lines varied in hEGF content but seeds within each line had a narrow range of hEGF accumulation. The EGF transgenic Line 5 produced in excess of 100 μg hEGF per gm dry seed weight, a level calculated to be much in excess of potential therapeutic requirements. By comparison, yeast stains have been used as an expression system for both hEGF and mouse EGF with the highest levels produced being from a multicopy insert *Pichia pastoris* clone secreting 49 μg EGF/ml. In both the mouse and hEGF yeast production systems, truncated versions of the EGF were detected.

The hEGF soybeans and non-transgenic soybeans were evaluated to determine the biochemical authenticity of the soybean-produced EGF protein. Using 1D SDS/PAGE and parallel immunoblots probed with anti-EGF, the soluble low molecular weight (<10 kDa) seed proteins and the Mr of the soybean-produced hEGF was evaluated. The total protein polypeptide of the hEGF expressing lines appeared to be identical to the standard parental control (See FIG. 2). Immunoblots of the 1D SDS/PAGE probed with anti-EGF showed a lack of an immunoreactive band in the non-transgenic soybean seed control and recognized a 6 kDa Mr band in the hEGF expressing Lines 5 and 4. The soybean-produced hEGF has the same apparent Mr as authentic recombinant hEGF fractioned in an adjacent lane (see FIG. 3). To further assess the soybean-synthesized hEGF the seed lysates were enriched in low Mr total proteins and concentrated. The crude low Mr proteins were reduced, alkylated, and cleaved with trypsin prior to analysis by mass spectrometry. The resulting data was queried with the hEGF sequence and exact matches for peptides encompassing the majority of the sequence of the complete mature hEGF protein were obtained (see FIG. 4). Together the data shows that transgenic soybeans successfully produced and accumulated hEGF that is the correct Mr, is immunoreactive with antibodies directed at authentic EGF in both ELISA and immunoblot assay, and that a majority mass spectrometry of fragments of the soybean-produced hEGF match the hEGF sequence.

Soybean-Milk is Compatible with EGF Bioactivity

Figure 5A:
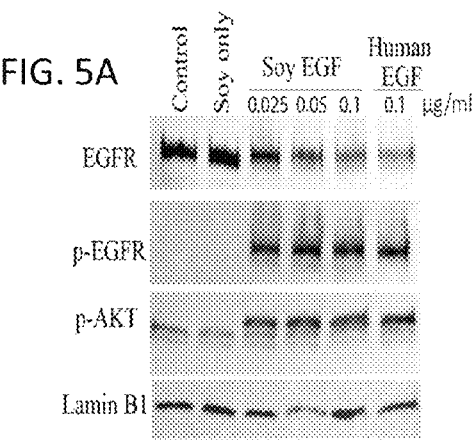
FIGS. 5A-5C show soybean produced EGF displayed comparable bioactivity to commercially available EGF.
Figure 5B:
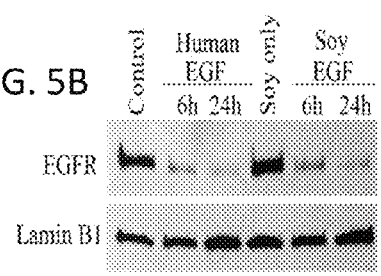
Figure 5C:
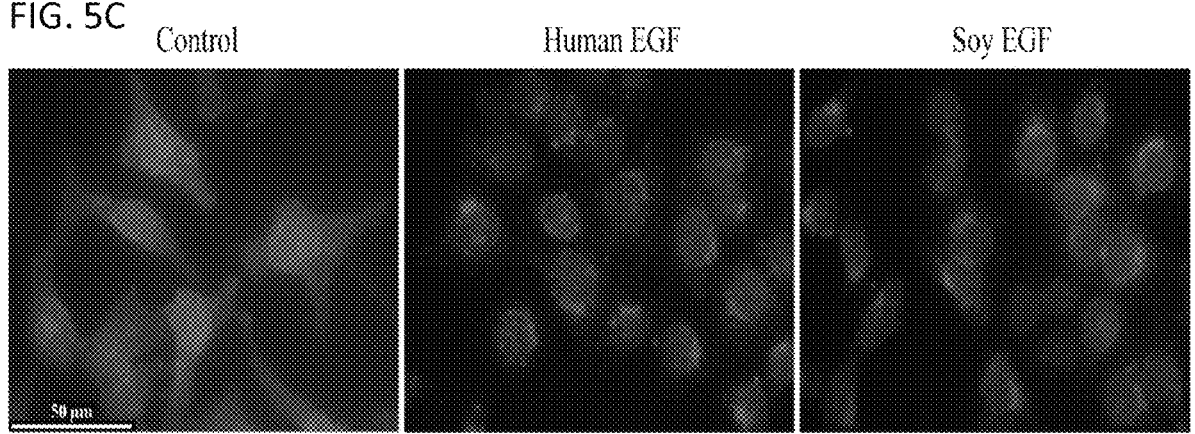

To evaluate the potential of EGF activity in soymilk delivery, commercial recombinant human EGF (rhEGF) was added as a supplement to soymilk and the intrinsic activity of the EGF was tested with a HeLa cell assay. FIG. 5 shows the effects of soymilk on the display of the EGF receptor (EGFR) on Hela cells and the effect of commercial rhEGF supplement to soymilk. Soymilk does not modify the display of EGFR on Hela cells showing that soymilk alone is biologically inactive. The binding of EGF to EGFR results in the decrease of displayed EGFR as it is internalized into the HeLa cells. Hela cells treated with commercially available recombinant rhEGF-supplemented soymilk display the same decrease in EGFR as cells treated with rhEGF in media without soymilk. Parallel time-course experiments show that the effect of rhEGF binding to EFGR is rapid with a reduction of displayed EFGR occurring within 5 min of treatment and continuing out to at least 30 min. Together these assays show that at this time, soymilk has no apparent negative bioactivity with respect to both the binding of commercial rhEGF to the HeLa cell EGFR or the viability of the HeLa cells over the course of the assay.

Soybean-Synthesized hEGF is Bioactive

To assess the bioactivity of soybean-produced hEGF, samples were prepared from both ShEGF transgenic soybean lines and non-transgenic controls that were used to stimulate HeLa cells to induce EGFR internalization, degradation and phosphorylation. As shown in FIG. 5, soybean-produced hEGF induces the internalization, degradation and phosphorylation of EGFR that is indistinguishable from the bioactivity of commercial rhEGF delivered in control samples. In contrast, samples prepared from control non-transgenic soybeans exhibited no apparent bioactivity showing the degradation and phosphorylation of EGFR is the result of EGF binding of either commercial rhEGF added to the media or from the hEGF produced by the transgenic soybeans. Together these results show that at this time, non-transgenic soybean seeds have no intrinsic EGF-mimic activity able to induce EGFR degradation or phosphorylation, while soybeans producing hEGF have identical activity in comparison to commercial rhEGF.

Synthesis of hEGF does not Affect Overt Soybean Seed Composition

To test for potential collateral composition in the hEGF-producing soybeans, the ShEGF transgenic and non-transgenic control soybeans were analyzed by non-targeted proteomics and metabolomics. Among the significant proteins identified include various well-documented allergens and anti-metabolite proteins. A comparison of standard soybeans with hEGF-producing soybean lines showed that there was no significant difference (p=0.01) between non-transgenic control and ShEGF transgenic soybeans aside from the targeted production of hEGF for any other proteins of concern. This data is available in PRIDE partner repository with the dataset identifier PXD003326 and 10.6019/PXD003326.

Non-targeted small molecule metabolomics was used to conduct a parallel analysis of the non-transgenic and hEGF soybeans. Again there were insignificant differences between non-transgenic soybean seeds and the ShEGF transgenic seeds (see FIG. 6) with one notable exception. Soybean highly regulates sulfur availability and its allocation into protein. From a nutritional perspective soybean is considered a somewhat sulfur-deficient crop. There have been a number of biotechnology experiments to increase sulfur content be either modifying assimilation and biosynthesis pathways leading to methionine or over-expressing high-methionine proteins such as Maize zeins. Modifying sulfur by pathway or competition has an effect on sulfur-responsive proteins including the Bowman-Birk trypsin inhibitor (BBI) and beta chain of the storage protein conglycinin. EGF is a high sulfur content protein that broadly mimics BBI as a small globular protein synthesized by the ER and presumptively competing for sulfur amino acid charge tRNA. Expressing hEGF in soybean has an effect on metabolites involved in sulfur amino acid metabolism that is consistent with producing a protein of EGF's composition. Among the assayed molecules of particular note is the soybean molecule Genistein, an isoflavone that has been shown to affect the activity of tyrosine phosphatase in the signal cascade associated with EGF signaling. Genistein levels were determined to be the same in both the non-transgenic and hEGF-expressing soybean lines. This, too, helps demonstrate that the expression of hEGF in soybeans does not produce any incidental collateral consequences of concern for its potential therapeutic use.

Example 1

The following Example describes non-limiting methods associated with the present invention.

Transgenic EGF Soybean Seeds

Epidermal growth factor protein from humans was produced in soybean seeds by constructing a plant gene expression cassette that involved a synthetic codon optimized EGF nucleotide sequence of SEQ ID NO.: 1, with corresponding amino acid sequence of SEQ ID NO: 12 (FIG. 7B) (utilizing hEGF nucleotide sequence of SEQ ID NO: 23 with corresponding encoded amino acid sequence of SEQ ID NO: 35 as shown in FIG. 7A). This 162 bp open reading frame was placed in-frame behind a 42-amino acid endoplasmic reticulum (ER) signal sequence from the *Arabidopsis* chitinase gene. The ER-directed EGF encoding open reading frame was developmentally regulated by the strong seed-specific storage protein glycinin regulatory elements. The entire seed specific cassette to direct EGF production was placed in a vector containing the hygromycin resistance gene under the strong constitutive expression of the potato ubiquitin 3 regulatory elements as previously described (Schmidt M A, Herman E M. The Collateral Protein Compensation Mechanism Can Be Exploited To Enhance Foreign Protein Accumulation In Soybean Seeds. Plant Biotechnol J. 2008; 6: 832-842; Schmidt M A, Herman EM. A RNAi knockdown of soybean 24 kda oleosin results in the formation of micro-oil bodies that aggregate to form large complexes of oil bodies and ER containing caleosin. Mol Plant. 2008; 1: 910-924; Schmidt M A, Parrott W A, Hildebrand D F, Berg R H, Cooksey A, Pendarvis K, et al. Transgenic soybean seeds accumulating β-carotene exhibit the collateral enhancements of high oleate and high protein content traits. Plant Biotechnol J. 2015; 13: 590-600). The result plasmid pGLY::ShEGF was sequenced using a glycinin promoter primer (5' TCATTCAC CTTCCTCTCTTC 3; (SEQ ID NO: 40) to ensure the EGF open reading frame was placed correctly between the regulatory elements. Somatic soybean (*Glycine max* L. Merrill cv Jack (wild type)) embryos were transformed via biolistics using 30 mg/L hygromycin B selection and regenerated as previously described (Schmidt M A, Tucker D M, Cahoon E B, Parrott W A. Towards normalization of soybean somatic embryo maturation. Plant Cell Rep. 2004; 24: 383-391). Embryos from resistant lines were analyzed by genomic PCR to confirm the presence of inserted hygromycin cassette using primers specific to the hygromycin gene (HygF 5'CTCACTAT-TCCTTTGCCCTC3'; (SEQ ID NO: 41) and HygR 5'CTGACCTATTGCATCTCCCG3'; (SEQ ID NO: 42), cetyl trimethyl ammonium bromide (CTAB) extraction genomic DNA isolation and the following amplification conditions: 150 ng genomic DNA in 25 µl total reaction containing 200 nM primers and 3 U Taq polymerase (NEB) and the following cycling parameters (initial 95° C. 4 min then 45 cycles of 95° C. 30 s, 55° C. 45 s, 72° C. 90 s; followed by a final extension of 72° C. 7 min). Dry seeds from two successive generations of PCR positive plants were analyzed by ELISA for the expression of EGF protein until all 7 lines were confirmed to be homozygous. EGF transgenic soybean plants along with non-transgenic control wild type cultivar plants were grown side by side in a greenhouse at 25° C. under 16 h daylight with 1000 µm−2/s.

As previously discussed, the present invention features compositions comprising nucleic acid sequence, SEQ ID NO: 1 of Table 1 below. The vector of SEQ ID NO: 1 comprises a modified hEGF gene (the sequence within SEQ ID NO: 1 that encodes hEGF is outlined). The optimized hEGF nucleic acid sequence is not limited to SEQ ID NO: 1 and comprises a nucleic acid that encodes a peptide of interest.

In some embodiments, the nucleic acid is at least about 90% identical to SEQ ID NO: 1. In some embodiments, the nucleic acid is at least about 93% identical to SEQ ID NO: 1. In some embodiments, the nucleic acid sequence is at least about 95% identical to SEQ ID NO: 1. In some embodiments, the nucleic acid sequence is at least about 98%© identical to SEQ ID NO: 1. In some embodiments, the nucleic acid sequence is at least about 99%© identical to SEQ ID NO: 1. Non-limiting examples of such nucleic acid sequences can be found in Table 1 below. For example, SEQ ID NO: 2 and SEQ ID NO: 7 are sequences for a modified hEGF that is about 99% identical to SEQ ID NO: 1. SEQ ID NO: 3 and SEQ ID NO: 8 are sequences for a modified EGF that is about 98% identical to SEQ ID NO: 1; SEQ ID NO: 4 and SEQ ID NO: 9 are sequences for a modified EGF that is about 95%© identical to SEQ ID NO: 1 (note that the bold letters in Table 1 are nucleotide substitutions as compared to SEQ ID NO: 1, and the codon underlined).

TABLE 1

Examples of Nucleic Acid Sequence Identity ≥ 90% to SEQ ID NO: 1

| Seq ID NO | Description | Nucleic Acid Sequence | % Alignment to SEQ ID NO: 1 |
|---|---|---|---|
| 1 | Optimized EGF sequence for soybean transformation | tctctttcttcagccgaaaattccgatagtgagtgtccactc tcccatgatgactattgtttgcacgacagagtttgcatgtat attgaagctttggataagtacgcatgtaactgcgttgtgg gatatatcggtgaaagatgccaatacagggacctcaaa tggtgggagctgagataa | 100 |
| 2 | Optimized EGF sequence for soybean transformation with 2 base substitution for 99% sequence identity to Seq ID 1 | tctctttcttcagccgaaacttccgatagtgagtgtccactc tcccatgatggctattgtttgcacgacggagttcgcatgta tattgaagctttggataagtacgcatgtaactgcgttgtgg gatatatcggtgaaagatgccaatacagggacctcaaa tggtgggagctgagataa | 99 |
| 3 | Optimized EGF sequence for soybean transformation with 4 base substitution for 98% sequence identity to Seq ID 1 | tctctttcttcagccgaaaactccgctagtgagtgtccact ctcccatgatggctattgtttgcacgacggagttcgcatgt atattgaagctttggataagtacgcatataactgcgttgtg ggatatatcggtgaaagatgccaatacagggacctcaa atggtgggagctgagataa | 98 |

TABLE 1-continued

Examples of Nucleic Acid Sequence Identity ≥ 90% to SEQ ID NO: 1

| Seq ID NO | Description | Nucleic Acid Sequence | % Alignment to SEQ ID NO: 1 |
|---|---|---|---|
| 4 | Optimized EGF sequence for soybean transformation with 9 base substitution for 95% sequence identity to Seq ID 1 | tctctttcttcagccgaaaactccgctagtgagtgttcact ctcccatgatggcgattgtttgcacgacggagttcgcatg tatattgaagctttggataagtacgcatataactgcgttgt ggaatatatcggtgaaagaggccaatacagggacctc aaacggtgggagctgagataa | 95 |
| 5 | Optimized EGF sequence for soybean transformation with 13 base substitution for 93% sequence identity to Seq ID 1 | tctctttcttcagccgaaaactccgctattgagtgttcactc tcccctgatggcgattgtttgcacgacggagttcgcatgt atattgaagctttgtataagtacgcatataactgcgttgtg gaatatatcggtgaaagaggccaatacaggaacctca aacggtgggagctgagataa | 93 |
| 6 | Optimized EGF sequence for soybean transformation with 18 base substitution for 90% sequence identity to Seq ID 1 | tctcttcttcagccgaaaactccgctattgagtgttcactc tcccctgatggcgattgtttgcaagacgtagttcgcatgt atagtgaagctttgtataagtacgcatataactgcgttgtg gaatatctcggtgaaagaggccaatacaggaacctca aacggtggaagctgagataa | 90 |
| 7 | Optimized EGF sequence for soybean transformation with 2 base substitution for 99% sequence identity to Seq ID 1 | tctctttcttcagccgaaaatcccgatagtgagtgtccact ctgccatgctggctattgttcgcacgacggagtttgcatgt atattgtagctgtggataagtacgcatgtaactgcgctgt gggatatatcggtgcaagatgccaatacagcgacctca aatggtgggacccgagataa | 99 |
| 8 | Optimized EGF sequence for soybean transformation with 4 base substitution for 98% sequence identity to Seq ID 1 | tctctttcttcagccgaaaatcccgatcgtgagtgtccact ctgccatgctggctattgttcgcacgacggagtttgcatgt atattgtagctgtggataagtacgcatgtaactgcgctgt gggatatcggtgcaagatgccaatacagcgacctca aatggtgggacccgagataa | 98 |
| 9 | Optimized EGF sequence for soybean transformation with 9 base substitution for 95% sequence identity to Seq ID 1 | tctctttcttcagccgaaaatcccgatcgtgagtgtccact ctgccatgctggctattgttcgcacgacggagtttgcatgt atattgtagctgtggataagtacgcatgtaactgcgctgt gggatatatcggtgcaagatgccaatacagcgacctca aatggtggggaccccgagataa | 95 |
| 10 | Optimized EGF sequence for soybean transformation with 13 base substitution for 93% sequence identity to Seq ID 1 | tctctttcttcagccgaaaatcccgatcgtgcgtgtccact ctgccatgctgtctattgttcgcacgacggactttgcatgt atattgtagctgtggataagtacgcatgtaactgcgctgt gggatatatcggtgcaagatgccaatacagcgacctca aatggtgggaccccgagataa | 93 |
| 11 | Optimized EGF sequence for soybean transformation with 18 base substitution for 90% sequence identity to Seq ID 1 | tctctttcttcagccgaaaatcccgatcgtgcgtgtctact ctgccatgctgtctattgttcgcacgacagagtttgcatgt atattgtagctgtggataagtactcatgtaactgcgctgtg ggatgtatcggtgcaagatgccaatacagcgacctcaa ttggtgggagccgagataa | 90 |

Bold letters are nucleotide substitutions within a codon; the respective codon is underlined The vector comprises a nucleic acid that encodes a peptide of interest. In some embodiments, the nucleic acid sequence is at least about 90% identical to SEQ ID NO: 1. In some embodiments, the nucleic acid sequence is at least about 93% identical to SEQ ID NO: 1. In some embodiments, the nucleic acid sequence is at least about 95% identical to SEQ ID NO: 1. In some embodiments, the nucleic acid sequence is at least about 98% identical to SEQ ID NO: 1. In some embodiments, the nucleic acid sequence is at least about 99% identical to SEQ ID NO: 1. Non-limiting examples of resulting amino acid sequences encoded by such nucleic acid sequences can be found in Table 2 below. For example, SEQ ID NO: 12 and SEQ ID NO: 18 are amino acid sequences encoded by modified hEGF polynucleotide sequences of Seq ID NO: 2 and SEQ ID NO: 6, respectively, that are about 99% identical to SEQ ID NO: 1 (note that the bold letters in Table 2 are amino acid substitutions as compared to SEQ ID NO: 12).

TABLE 2

Examples of Amino Acid Sequence with Nucleic Acid Identity ≥90%

| Seq ID NO | Description | Amino Acid Sequence | % Alignment to Seq ID NO: 1 |
|---|---|---|---|
| 12 | Optimized EGF sequence for soybean transformation | SLSSAENSDSECPLSHDGYCLHDGVCMYIEAL DKYACNCVVGYIGERCQYRDLKWWELR | 100 |

TABLE 2-continued

Examples of Amino Acid Sequence with Nucleic Acid Identity ≥90%

| Seq ID NO | Description | Amino Acid Sequence | % Alignment to Seq ID NO: 1 |
|---|---|---|---|
| 13 | Optimized EGF sequence for soybean transformation with 2 base substitution for 99% sequence identity to Seq ID 1 | SLSSAETSDSECPLSHDGYCLHDGVRMYIEALD KYACNCVVGYIGERQYRDLKWWELR | 99 |
| 14 | Optimized EGF sequence for soybean transformation with 4 base substitution for 98% sequence identity to Seq ID 1 | SLSSAETSASECPLSHDGYCLHDGVRMYIEALD KYAYNCVVGYIGERCQYRDLKWWELR | 98 |
| 15 | Optimized EGF sequence for soybean transformation with 9 base substitution for 95% sequence identity to Seq ID 1 | SLSSAETSASECSLSHDGDCLHDGVRMYIEAL DKYAYNCVVEYIGERGQYRDLKRWELR | 95 |
| 16 | Optimized EGF sequence for soybean transformation with 13 base substitution for 93% sequence identity to Seq ID 1 | SLSSAETSAIECSLSPDGDCLHDGVRMYIEALY KYAYNCVVEYIGERGQYRNLKRWELR | 93 |
| 17 | Optimized EGF sequence for soybean transformation with 18 base substitution for 90% sequence identity to Seq ID 1 | SLSSAETSAIECSLSPDGDCLQDVVRMYSEALY KYAYNCVVEYLGERGQYRNLKRWKLR | 90 |
| 18 | Optimized EGF sequence for soybean transformation with 2 base substitution for 99% sequence identity to Seq ID 1 | SLSSAENADSECPLSHDGYCLHDGVCMYIVAL DKYACNCVVGYIGERCQYRDLKWWELR | 99 |
| 19 | Optimized EGF sequence for soybean transformation with 4 base substitution for 98% sequence identity to Seq ID 1 | SLSSAENADRECPLSHAGYCLHDGVCMYIVAL DKYACNCVVGYIGERCQYRDLKWWELR | 98 |
| 20 | Optimized EGF sequence for soybean transformation with 9 base substitution for 95% sequence identity to Seq ID 1 | SLSSAENADRECPLCHAGYCSHDGVCMYIVAL DKYACNCAVGYIGERCQYSDLKWWEPR | 95 |
| 21 | Optimized EGF sequence for soybean transformation with 13 base substitution for 93% sequence identity to Seq ID 1 | SLSSAENADRACPLCHAVYCSHDGVCMYIVAV DKYACNCAVGYIGARCQYSDLKWWEPR | 93 |
| 22 | Optimized EGF sequence for soybean transformation with 18 base substitution for 93% sequence identity to Seq ID 1 | SLSSAENADRACLLCHAVYCSHDRVCMYIVAV DKYSCNCAVGCIGARCQYSDLNWWEPR | 90 |

Bold letters are nucleotide substitutions within a codon; the respective codon is underlined.

The present invention also features compositions comprising nucleic acid SEQ ID NO: 26 of Table 3 below. The vector of SEQ ID NO: 1 comprises a modified hEGF gene comprising a modified polynucleotide for the protein-coding region of hEGF, SEQ ID NO: 26 (the sequence within SEQ ID NO: 1 that encodes hEGF is outlined). The optimized hEGF nucleic acid protein-coding sequence is not limited to SEQ ID NO: 26 and comprises a nucleic acid that encodes a peptide of interest.

In some embodiments, the hEGF protein-coding nucleotide sequence is at least 90% identical to SEQ ID NO: 26. In some embodiments, the nucleic acid is at least 93% identical to SEQ ID NO: 26. In some embodiments, the nucleic acid is at least 95% identical to SEQ ID NO: 26. In some embodiments, the nucleic acid is at least 98% identical to SEQ ID NO: 26. In some embodiments, the nucleic acid is at least 99%© identical to SEQ ID NO: 26. Non-limiting examples of such nucleic acid sequences can be found in Table 3 below. For example, SEQ ID NO: 27 is a sequence for a modified hEGF that is about 99% identical to SEQ ID NO: 26. SEQ ID NO: 28 is a sequence for a modified EGF that is about 98% identical to SEQ ID NO: 26; SEQ ID NO: 29 is a sequence for a modified EGF that is about 95% identical to SEQ ID NO: 26 (note that the bold letters in Table 3 are nucleotide substitutions as compared to SEQ ID NO: 26, and the codon underlined).

TABLE 3

Examples of Nucleic Acid Sequence Identity ≥ 90% to Coding Region of SEQ ID NO: 26

| Seq ID | Description | Nucleic Acid Sequence | % Alignment to SEQ ID NO: 26 |
|---|---|---|---|
| 26 | Coding Region of SEQ ID: 1 | aattccgatagtgagtgtccactctcccatgatggctattg tttgcacgacggagtttgc*atg*tatattgaagcttggata agtacgcatgtaactgcgttgtgggatatatcggtgaaa gatgccaatacagggacctcaaatggtgggagctgag at*aa* | 100 |
| 27 | Coding Region of SEQ ID: 1 with 2 base substitution for 99% sequence identity to Seq ID 26 | <u>act</u>ccgatagtgagtgtccactctcccatgatggctattg tttgcacgacggagtt<u>cgc</u>*atg*tatattgaagctttggata agtacgcatgtaactgcgttgtgggatatatcggtgaaa gatgccaatacagggacctcaaatggtgggagctgag at*aa* | 99 |
| 28 | Coding Region of SEQ ID: 1 with 4 base substitution for 98% sequence identity to Seq ID 26 | <u>aac</u>ccg<u>ct</u>agtgagtgtccactctcccatgatggctatt gtttgcacgacggagtt<u>cgc</u>*atg*tatattgaagctttggat aagtacgca<u>tat</u>aactgcgttgtgggatatatcggtgaa acatgccaatacagggacctcaaatggtgggagctga gat*aa* | 98 |
| 29 | Coding Region of SEQ ID: 1 with 9 base substitution for 95% sequence identity to Seq ID 26 | <u>aac</u>ccg<u>ct</u>agtgagtgt<u>tc</u>actctcccatgata<u>gatt</u> gtttgcacgacggagtt<u>cgc</u>*atg*tatattgaagctttggat aagtacgca<u>tat</u>aactgcgttgtg<u>aa</u>tatatcggtgaa aga<u>gg</u>ccaatacagggacctcaaa<u>cgg</u>tgggagctg agat*aa* | 95 |
| 30 | Coding Region of SEQ ID: 1 with 12 base substitution for 93% sequence identity to Seq ID 26 | <u>aac</u>ccg<u>ct</u>at<u>t</u>gagtgt<u>tc</u>actctcc<u>cct</u>gatggc<u>g</u>attg tttgcacgacggagtt<u>cgc</u>*atg*tatattgaagctttgtata agtacgca<u>tat</u>aactgcgttgtg<u>aa</u>tatatcggtgaaa ga<u>gg</u>ccaatacaggaacctcaaa<u>cgg</u>tgggagctga gat*aa* | 93 |
| 31 | Coding Region of SEQ ID: 1 with 17 base substitution for 90% sequence identity to Seq ID 26 | <u>aac</u>ccg<u>ct</u>at<u>t</u>gagtgt<u>tc</u>actctcc<u>cct</u>gatggc<u>g</u>attg tttgc<u>aa</u>gacg<u>t</u>agtt<u>cgc</u>*atg*tata<u>gt</u>gaagctttg<u>t</u>at<u>a</u> agtacgca<u>tat</u>aactgcgttgtg<u>aa</u>tat<u>ct</u>cggtgaaa ga<u>gg</u>ccaatacaggaacctcaaa<u>cgg</u>tgg<u>aa</u>gctga gat*aa* | 90 |

Bold letters are nucleotide substitutions within a codon; the respective codon is underlined The present invention also features compositions comprising nucleic acid sequence, SEQ ID NO: 32 of Table 4 below. The vector of SEQ ID NO: 1 comprises a modified hEGF gene comprising a polynucleotide for the non-hEGF protein coding region, SEQ ID NO: 32. The non-hEGF protein coding sequence of the optimized hEGF nucleotide is not limited to SEQ ID NO: 32. In some embodiments, the 3' end of SEQ ID NO: 32 is operatively coupled to the 5' end of SEQ ID NO: 26.

In some embodiments, the non-hEGF protein coding nucleotide sequence is at least 90% identical to SEQ ID NO: 32. Non-limiting examples of such nucleic acid sequences can be found in Table 4 below. For example, SEQ ID NO: 33 is a sequence that is at least 90% (<100%) identical to SEQ ID NO: 32 (note that the bold letters in Table 4 are nucleotide substitutions as compared to SEQ ID NO: 32, and the codon underlined).

EGF Quantification

Total soluble protein was extracted from dry soybean seeds as described previously (Schmidt M A, Herman E M. The Collateral Protein Compensation Mechanism Can Be Exploited To Enhance Foreign Protein Accumulation In Soybean Seeds. Plant Biotechnol J. 2008; 6: 832-842; Schmidt M A, Herman E M. A RNAi knockdown of soybean 24 kda oleosin results in the formation of micro-oil bodies that aggregate to form large complexes of oil bodies and ER containing caleosin. Mol Plant. 2008; 1: 910-924) from all 7 lines of pGLY::ShEGF transgenic plants along with non-transgenic seeds as a negative control. EGF was quantitated by commercially available hEGF ELISA assay (Quantikine ELISA kit from R&D systems, Minneapolis Minn.) according to the manufacturer's instructions. The provided positive control was used to create a standard curve in order to determine the amount of EGF in each soybean protein

TABLE 4

Examples of Nucleic Acid Sequence Identity ≥ 90% to Non-hEGF Protein Coding Region of SEQ ID NO: 32

| Seq ID | Description | Nucleic Acid Sequence | % Alignment to SEQ ID NO: 32 |
|---|---|---|---|
| 32 | Optimized non-hEGF protein coding region nucleic acid sequence | tctctttcttcagccgaa | 100 |
| 33 | Optimized non-hEGF protein coding sequence with 1 base substitution for at least 90% sequence identity to Seq ID 32 | tctttttcttcagccgaa | ≥ 95 < 100 |
| 34 | Optimized non-hEGF protein coding region sequence with 2 base substitution for at least 90% sequence identity to Seq ID 32 | tctttttcttaagccgaa | ≥ 90 < 95 |

Bold letters are nucleotide substitutions within a codon; the respective codon is underlined EGF Detection Via Immunoblot Total soluble protein was extracted from dry seeds of two homozygous EGF lines and a non-transgenic control by repeated acetone washes followed by acetone precipitation with the protein pellet dissolved in water. Proteins with molecular weight 10 kDa and under were isolated by separately passing each extract through an Amicon Ultra centrifugal filter (Merck. Kenil-worth NJ). The samples were each suspended in sample buffer (50 mM Tris HCL, pH6.8 2% SDS (w/v), 0.7 M β-mercaptoethanol, 0.1% (w/v) bromphenol blue and 10% (v/v) glycerol) and then denaturated 5 min 95° C. Protein content was determined by Bradford assay. A 15% SDS-PAGE gel was used to separate 30 μg protein for each of the three samples: negative control wild type. Lines 4 and 5 of EGF transgenic soybean dry seeds. Commercially available hEGF (Gibco, Life Technologies, United Kingdom) was used at 0.5 μg as positive control. Gel was electroblotted onto Immobilon P transfer membrane (Millipore, Bedford Mass.) and blocked with 3% milk solution in TBS for at least 1 hr. Primary antibody was a commercially available anti-EGF (Calbiochem, San Diego Calif.) and was used in a 1:100 ratio in 3% BSA-TBS buffer overnight at room temperature. After 3 washes of 15 mins each with TBS buffer, the blot was incubated with a 1:10,000 ratio in TBS of secondary antibody anti-rabbit IgG Fabspecific alkaline phosphatase conjugate (Sigma, St. Louis Mo.). After 3 washes, the presence of the EGF protein was detected by using a color substrate (BCIP/NBT: final concentrations 0.02% (w/v) 5-bromo-4-chloro-3-indoyl phosphate and 0.03% (w/v) nitro blue tetrazolium in 70% (v/v) dementhylformadmide) (KPL, Gaithersburg Mass.).

extract. Each homozygote EGF transgenic line was assayed with three biological replicates and results displayed as mean+/−standard error.

Seed Proteome Composition Analysis

Total soluble proteins were extracted, quantitated and suspended in sample loading buffer as previously described (Schmidt M A, Herman E M. The Collateral Protein Compensation Mechanism Can Be Exploited To Enhance Foreign Protein Accumulation In Soybean Seeds. Plant Biotechnol J. 2008; 6: 832-842; Schmidt M A, Herman E M. A RNAi knockdown of soybean 24 kda oleosin results in the formation of micro-oil bodies that aggregate to form large complexes of oil bodies and ER containing caleosin. Mol Plant. 2008; 1: 910-924). Approximately 30 μg of protein extract from dry seeds of 4 homozygous EGF lines were separated on a 4-20% gradient SDS-PAGE gel (BioRad, Hercules Calif.) along with extract from a non-transgenic seed. The gel was subsequently stained with 0.1% (w/v) Coomassie Brilliant Blue R250 in 40% (v/v) methanol, 10% (v/v) acetic acid overnight and then de-stained for approximately 3 hrs in 40% methanol, 10% acetic acid with frequent solution changes.

Mass Spectrometry Analysis to Detect EGF in Soybean Samples

Total soluble protein was extracted from 3 biological EGF transgenic soybean dry seed samples, lines 4, 5 and 6. As described above, proteins with molecular weights lower than 10 kDa were concentrated using an Amicon Ultra centrifugal filter (Merck, Kenilworth N.J.). Non-transgenic seeds were used as a negative control and 5 μg commercially available EGF (as above in immunoblot section) was the positive control. Protein was precipitated by adjusting the solution to 20%© (v/v) trichloroacetic acid and allowed to sit at 4° C. overnight. Precipitated proteins were pelleted using centrifugation, washed twice with acetone and then dried using vacuum centrifugation. The commercial EGF was not filtered or precipitated, only dried. Dried pellets were rehydrated with the addition of 10 µl 100 mM dithreitol in 100 mM ammonium bicarbonate and placed at 85° C. for 5 minutes to reduce disulphide bonds. Samples were then alkylated with addition of 10 µl iodacetamide in 100 mM ammonium bromide and placed at room temperature in the dark for 30 minutes. Two µg trypsin in 200 µl 100 mM ammonium bromide was added to each samples and placed in 37° C. overnight for enzymatic digestion. Post trypsin digest samples were desalted using a peptide reverse phase microtrap (Michrom BioResources, Auburn Calif.), dried and ultimately resuspended in 2 µl of 2% (v/v) acetonitrile, 0.1% (v/v) for-mic acid. Separation of peptides was performed using a Dionex U3000 splitless nanoflow HPLC system operated at 333 nl minute using a gradient from 2-50% acetonitrile over 60 minutes, followed by a 15 minute wash with 95% acetonitrile and a 15 minute equilibration with 2% acetonitrile. The 018 column, an in-house prepared 75 µm by 15 cm reverse phase column packed with Halo 2.7 µm, 90 Å C18 material (MAC-MOD Analytical, Chadds Ford Pa.) was located in the ion source just before a silica emitter. A potential of 2100 volts was applied using a liquid junction between the column and emitter. A Thermo LTQ Velos Pro mass spectrometer using a nanospray Flex ion source was used to analyze the eluate from the U3000. Scan parameters for the LTQ Velos Pro were one MS scan followed by 10 MS/MS scans of the 5 most intense peaks. MS/MS scans were performed in pairs, a CID fragmentation scan followed a HOD fragmentation scan of the same precursor m/z. Dynamic exclusion was enabled with a mass exclusion time of 3 min and a repeat count of 1 within 30 sec of initial m/z measurement. Spectra were collected over the entirety of each 90 minute chromatography run. Raw mass spectra were converted to MGF format using MSConvert, part of the ProteoWizard software library (Kessner D, Chambers M, Burke R, Agus D, Mallick P. ProteoWizard: open source software for rapid proteomics tools development. Bioinformatics. 2008; 24: 2534-2536) Xltandem 2013.09.01.1 (Craig R, Beavis R C. TANDEM: matching proteins with tandem mass spectra. Bioinformatics. 2004; 20: 1466-1467) and OMSSA (Geer L Y, Markey S P, Kowalak J A, Wagner L, Xu M, Maynard D M, et al. Open mass spectrometry search algorithm. J Proteome Res. 2004; 3: 958-964) algorithms were employed via the University of Arizona High Performance Computing Center to perform spectrum matching. Precursor and fragment mass tolerance were set to 0.2 Daltons for both OMSSA and Mandem. Trypsin cleavage rules were used for both algorithms with up to 2 missed cleavages. Amino acid modifications search consisted of single and double oxidation of methionine, oxidation of praline, N-terminal acetylation, carbamidomethylation of cysteine, deamidation of asparagine and glutamine and phosphorylation of serine, threonine, and tyrosine. Ktandem xml and OMSSA xml results were filtered using Perl to remove any peptide matches with an E-value >0.05 as well as proteins identified by a single peptide sequence. The protein fasts database for *Glycine max* was downloaded on Aug. 5, 2015 from NCBI RefSeq with the addition of the EGF amino acid sequence. A randomized version of the *Glycine max* fasta was concatenated to the original as a way to assess dataset quality. The mass spectrometry proteo-mics data have been deposited to the ProteomeXchange Consortium (http://proteomecentral.proteomexchange.org) via the PRIDE partner repository (Guo J, Longshore S, Nair R, Warner B W. Retinoblastoma protein (pRb), but not p107 or p130, is required for maintenance of enterocyte quiescence and differentiation in small intestine. J Biol Chem. 2009; 284:134-40) with the dataset identifier PXD003326 and 10.6019/PXD003326.

Cell Culture, Western Blotting and Immunocytochemistry

Hela cells (obtained from American Tissue Culture Collection) were cultured in Minimum Essential Media (MEM) complemented with 10% Fetal Bovine Serum (FBS), 100 units/ml penicillin, and 100 µg/ml streptomycin. For western blotting assay, cells grown in 6-well plate were kept in serum free MEM media for 24 hours. Cells were then either kept in serum free medium (control) or stimulated with soymilk alone, soy EGF or commercial recombined hEGF for different time period as indicated. Cells were lysed by directly adding 1×SDS sample buffer (50 mM Tris-HCl, pH 6.8, 10% glycerol, 2% SDS and 5% 13-ME) to the cells after washing 3 times with 1×PBS. EGF bio-activity was determined via EGFR phosphorylation and down-stream AKT phosphorylation. Total EGFR was also measured since EGFR is known to undergo internalization when stimulated with EGF. Antibodies used in western blot are anti-p-EGFR (Tyr1068) (#2234, Cell Signaling Technology), anti-total EGFR (#06-847, Millipore), anti-p-AKT (#4060, Cell Signaling Technology) and anti-Lamin B1 (#13435, Cell Signaling Technology) [40]. For immunocytochemistry assay, cells were grown on coverslip in 6-well plate and kept in serum free media for 24 hours before stimulation, cells were then either kept in serum free media (control) or stimulated with human or soy EGF for 6 hours. Cells were washed with PBS and fixed with 4% formalin. EGFR was labeled using anti-EGFR antibody (#4267, Cell Signaling Technology) and detected with Alexa Fluor 594 Goat anti-rabbit IgG (#A11012, life technology). The cell nuclei were shown using mounting medium with DAPI (#H-1200, Vectorshield).

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and only for ease of review by the patent office and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A transgenic soybean producing a soluble, bioactive, endoplasmic reticulum (ER)-directed human epidermal growth factor (hEGF) protein, wherein the soybean plant is transformed with an artificial DNA construct to direct EGF production, the construct comprising operably associated components in the 5' to 3' direction of transcription:
   (a) a promoter that functions in soybean;
   (b) a nucleotide sequence that when translated encodes and ER signal peptide comprising SEQ ID NO: 24 operably linked to the 3' end of the promoter;
   (c) a polynucleotide operably linked to the 3' end of the sequence encoding the ER-signal peptide, wherein the polynucleotide comprises a sequence selected from the group consisting of SEQ ID NO: 1, SEQ ID NO: 26, or a sequence of at least 95% identical thereto, wherein the polynucleotide encodes a protein having hEGF activity, or a polynucleotide linked to the 3' end of the sequence encoding the ER-signal peptide, wherein the polynucleotide sequence encodes a protein of SEQ ID NO: 12 or a sequence that is at least about 90% identical thereto having hEGF activity;
   (d) a nucleotide sequence that when translated encodes an ER retention signal comprising SEQ ID NO: 25; and
   (e) a transcriptional termination sequence;
wherein the transgenic soybean directly exhibits bioactive hEFG, wherein bioactive hEGF is having hEGF-like activity comprising internalization of epidermal growth factor receptor (EGFR), phosphorylation of EGFR, and/or phosphorylation of AKT.

2. The transgenic soybean of claim 1, wherein the promoter is a seed-specific promoter.

3. The transgenic soybean of claim 2, wherein the promoter comprises a Glycinin (GLY) promoter or a Late embryonic abundant protein (LEA) promoter sequence.

4. A soymilk composition comprising soybean produced soluble, bioactive, endoplasmic reticulum (ER)-directed and ER-retained human epidermal growth factor (ShEGF) comprising a protein encoded by a polynucleotide with a sequence of SEQ ID NO: 1, SEQ ID NO: 26, or a sequence that is at least about 95% identical thereto, wherein said polynucleotide further comprises a nucleic acid encoding a signal peptide comprising SEQ ID NO: 24 fused in-frame to the ShEGF protein, wherein the encoded bioactive ShEGF protein has hEGF activity comprising internalization of epidermal growth factor receptor (EGFR), phosphorylation of EGFR, and/or phosphorylation of AKT comparable to activity derived from purified recombinant hEGF, and wherein the composition comprises the polynucleotide.

5. A method of producing a soluble and bioactive soybean-derived human epidermal growth factor (ShEGF) in a deliverable soymilk platform, said method comprising: constructing a seed-specific cassette to direct production of a soluble, bioactive, and endoplasmic reticulum (ER)-directed and ER-retained protein encoded by SEQ ID NO: 1, SEQ ID NO: 26, or a sequence of at least about 95% identical thereto and said protein further comprising at its N-terminus a signal peptide comprising SEQ ID NO: 24, in a transgenic soybean comprising a transgene comprising a polynucleotide with a sequence of SEQ ID NO: 1, SEQ ID NO: 26 or a sequence that is at least about 95% identical thereto, wherein the soluble and bioactive protein encoded by SEQ ID NO: 1, SEQ ID NO: 26 or a sequence that is at least about 95% identical thereto, is a soluble and bioactive hEGF, or a protein having hEGT activity comprising internalization of epidermal growth factor receptor (EGFR), phosphorylation of EGFR, and/or phosphorylation of AKT.

* * * * *